United States Patent [19]

Platzek et al.

[11] Patent Number: 5,679,852
[45] Date of Patent: Oct. 21, 1997

[54] PROCESS FOR THE PRODUCTION OF DTPA-MONOAMIDES OF THE CENTRAL CARBOXYLIC ACID AND THEIR USE AS PHARMACEUTICAL AGENTS

[75] Inventors: Johannes Platzek; Ulrich Niedballa; Peter Mareski; Bernd Raduchel, all of Berlin, Germany

[73] Assignee: Schering Aktiengesellschaft, Berlin, Germany

[21] Appl. No.: 460,119

[22] Filed: Jun. 2, 1995

[51] Int. Cl.$^6$ .................................................. C07C 231/02
[52] U.S. Cl. ................ 564/138; 548/339.1; 548/339.5; 548/497; 562/565
[58] Field of Search ................. 564/138; 562/565; 548/339.1, 339.5, 497

[56] References Cited

U.S. PATENT DOCUMENTS

| | | | |
|---|---|---|---|
| 4,647,447 | 3/1987 | Gries et al. | 424/9 |
| 4,675,442 | 6/1987 | Besecke et al. | 564/135 |
| 4,925,804 | 5/1990 | Hale et al. | 436/501 |
| 4,957,939 | 9/1990 | Gries et al. | 514/492 |
| 4,963,344 | 10/1990 | Gries et al. | 424/9 |
| 5,017,533 | 5/1991 | Newkirk et al. | 501/127 |
| 5,362,475 | 11/1994 | Gries et al. | 424/9 |
| 5,376,357 | 12/1994 | Rajagopalan et al. | 424/9 |
| 5,399,340 | 3/1995 | Radüchel et al. | 424/9 |

OTHER PUBLICATIONS

Westerberg, et al., J. Med. Chem. 32, 236–243 (1989). 1989.
Ma et al., "Use of the Gamma-Ray Perturbed Angular Correlation (PAC) Technique... etc.", Pharm.Res. vol. 10, No. 2, 1993, pp. 252–257.
Maisano et al., "Coupling of DTPA to Proteins: A Critical Analysis of the Cyclic... etc.", Bioconjugate Chem. 1992, 3, pp. 212–217.
Steven et al., "Competitive Inhibition of a Tumour Cell Surface...", J. Enzyme Inhibition. 1990, vol. 4, pp. 63–73.

*Primary Examiner*—Johann Richter
*Assistant Examiner*—Laura R. Cross
*Attorney, Agent, or Firm*—Millen, White, Zelano & Branigan, P.C.

[57] ABSTRACT

A process for the production of of general formula I diethylenetriaminepentacarboxylic acid monoamide derivatives

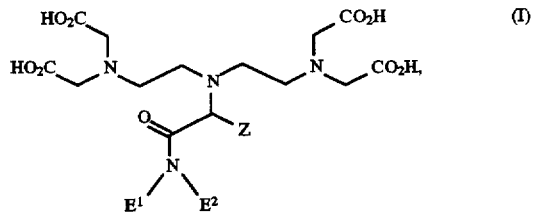

in which $E^1$, $E^2$ and Z have varying meanings.

14 Claims, No Drawings

PROCESS FOR THE PRODUCTION OF DTPA-MONOAMIDES OF THE CENTRAL CARBOXYLIC ACID AND THEIR USE AS PHARMACEUTICAL AGENTS

The invention relates to a process for the production of diethylenetriaminepentacarboxylic acid monoamide compounds of the central carboxylic acid as well as the use of compounds, produced by the described process, for the production of agents for NMR diagnosis and diagnostic radiology.

BACKGROUND OF THE INVENTION

Diethylenetriaminepentaacetic acid (DTPA) and derivatives of this compound are widely used in medicine and technology, both in free form and in the form of their complex compounds. In EP 71564 B1, i.a., the meglumine salt of the gadolinium(III) complex of diethylenetriaminepentaacetic acid (DTPA) is described as a contrast medium for NMR tomography. A preparation which contains this complex was approved worldwide under the name Magnevist® as the first NMR contrast medium. After intravenous administration, this contrast medium spreads extracellularly and is excreted renally by glomerular secretion. A passage of intact cell membranes is practically not observed. Magnevist® is especially well-suited for the visualization of pathological areas (e.g., inflammations, tumors).

In the past, there have been many attempts to link DTPA with functional radicals which exhibit an organ or cell specificity to achieve in this way a contrast medium concentration in certain types of tissue.

Within the prior art, DTPA derivatives were proposed for radiodiagnostic investigations, in which the central acetic acid unit is to be linked by an amide linkage with a molecular fragment, which can cause an organ-, tissue- or cell-specificity. But the described processes for the production of these compounds exhibit a number of drawbacks.

Hnatowich (J. Nucl. Med. 22: 810, 1981) describes the coupling of octadecylamine to DTPA-bis-anhydride by reaction of a bis-anhydride of DTPA. But the course of reaction of this synthesis is disputed.

Gruaz-Guyon et al. (Pept. 1990, Proc. Eur. Pept. Symp., 21st (1991), PP. 822–825), Goto et al. (Chem. Pharm. Bull. 39: 230, 1991), Steven et al. (J. Enzyme Inhib. 4: 63, 1990) and Hale et al. (U.S. Pat. No. 4,925,804) postulate a selective linkage of the central acetic acid unit, without presenting proof of this theory. Based on the structure of the feedstock pictured below, the authors assume that the linkage can take place only on the free central carboxylic acid unit of the bis-anhydride.

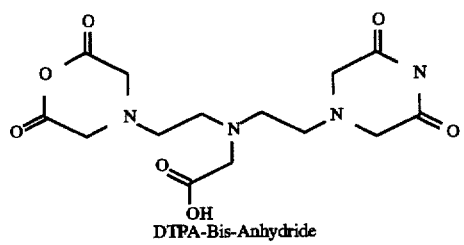

DTPA-Bis-Anhydride

In patent specifications WO 91/03261 and EP 263059 A1, however, exclusive linkages of the terminal acetic acid groups are obtained in the reaction of the bis-anhydride of the DTPA with amines analogously to Hnatowich. Gozzini (Bioconjugate Chem. 3: 212, 1992) describes complex product mixtures using this process for coupling to insulin, which substantiate that with the use of this process, bis-amides are also obtained as products despite stoichiometric use of feedstocks (bis-anhydride:amine=1:1).

Hnatowich himself makes no statements on the structure or homogeneity of his process product. Based on the comparatively drastic reaction conditions (several days of refluxing in chloroform, treatment with boiling water, recrystallization from boiling ethanol), moreover, this process is not suitable for coupling to sensitive amines, since both decomposition reactions of the amines and decompositions of the solvent (HCl elimination) occur. Further, the DTPA-bis-anhydride is poorly soluble, so that the process cannot take place in homogeneous solution.

Unlike the above-mentioned authors, Ma et al. (Pharm. Res. 10: 252, 1993) uses a pentakis(triethylammonium) derivative of DTPA for coupling the DTPA to amines. But the amide linkage is statistically dispersed in the product mixture corresponding to the distribution of the acetic acid functions of the feedstock (terminal:central=4:1).

SUMMARY OF THE INVENTION

An object of this invention is therefore to provide a novel process for the coupling of amines to the central carboxylic acid of DTPA, which proceeds specifically, which further can be performed under mild conditions and thus—by avoiding regroupings, racemizations and eliminations—is also suitable for the reaction of sensitive amines. This object is achieved by the invention described herein. Upon further study of the specification and appended claims, further objects and advantages of this invention will become apparent to those skilled in the art.

It has been found that compounds of general formula I

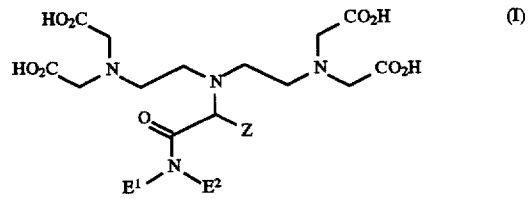

in which

Z, $E^1$, $E^2$ independently of one another, each stand for a hydrogen atom or a saturated or unsaturated, branched or straight-chain $C_1$–$C_{50}$ alkyl chain, wherein:

the chain or parts of this chain optionally can form a cyclic $C_5$–$C_8$ unit or a bicyclic $C_{10}$–$C_{14}$ unit;

the alkyl chain may also contain 0 to 10 oxygen and/or 0 to 2 sulfur atoms and/or 0 to 3 carbonyl, 0 to 1 thiocarbonyl, 0 to 2 imino, 0 to 2 phenylene, 0 to 1 3-indole, 0 to 1 methyl-imidazol-4-yl and/or 0 to 3 N-$R^3$ groups, and the alkyl chain may further be substituted by 0 to 2 phenyl, 0 to 2 pyridyl, 0 to 5 $R^2O$, 0 to 1 HS, 0 to 4 $R^2OOC$, 0 to 4 $R^2OOC$—$C_{1-4}$ alkyl and/or 0 to 1 $R^2(H)N$ groups, in which optionally present aromatic groups can be substituted zero to five times, independently of one another, by fluorine, $R^2O_2C$, $R^2OOC$—$C_{1-4}$ alkyl, $R^2(H)N$, $C_{1-4}$ alkyl-NH, $R^2NHOC$, $R^2CONH$, $O_2N$, $R^2O$, and/or $R^2$ groups, $R^2$ independently of one another, each stand for a hydrogen atom or a straight-chain or branched $C_1$–$C_4$ alkyl radical and $R^3$ independently of one another, each stand for a hydrogen atom or a straight-chain or branched, saturated or unsaturated $C_1$–$C_{30}$ alkyl radical, or $E^1$ and $E^2$ together with inclusion of the nitrogen atom, stand for a five- to eight-membered, saturated or unsaturated heterocycle, which optionally contains in the ring one to two additional nitrogen, oxygen, sulfur atoms and/or carbonyl groups, in which the HO and/or $H_2N$ and/or HS and/or HOOC group(s) optionally contained in $E^1$ and/or $E^2$ can be present in protected form and in which free carboxylic acid groups not used for complexing can also be present as salts with physiologically compatible inorganic and/or organic cations or as esters or amides, characterized in that a partially protected diethylenetriaminepentacarboxylic acid derivative according to general formula II

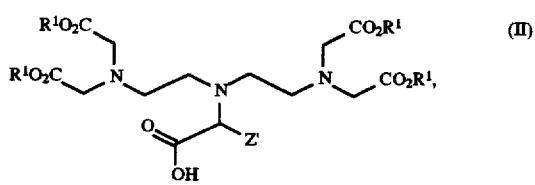

in which $R^1$ stands for a tert-butyl group or a benzyl group and Z' has the meaning of an optionally protected group Z, in which Z has the above-mentioned meaning, is reacted, optionally with the addition of an activating reagent, with an amine of general formula III

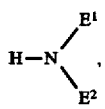

in which $E^1$ and $E^2$ have the above-mentioned meaning, and then the free acid of general formula I is produced by selective and mild cleavage of groups $R^1$, as well as the protective groups optionally contained in Z'.

The designations of terminal or central carboxylic acids in DTPA can be defined as follows:

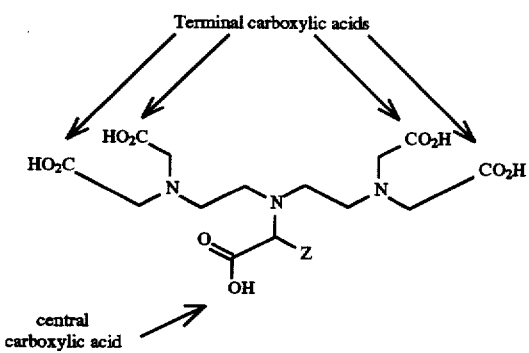

As groups $E^1$ or $E^2$, there can be mentioned as examples the hydrogen atom, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, cyclopentyl, cyclohexyl, cycloheptyl, cyclooctyl radicals, cyclohexenyl, cyclopentanone, cyclohexanol, cyclohexenol, 2-aminocycloheptane, 2-hydroxyethyl, 5-oxononyl, hex-5-enyl, icosa-19-enyl, 2-ethylhexyl, 2-ethoxyhexyl, phenyl, benzyl, naphthyl, imidazolyl, thiazolyl radicals, as well as radicals of formulae:

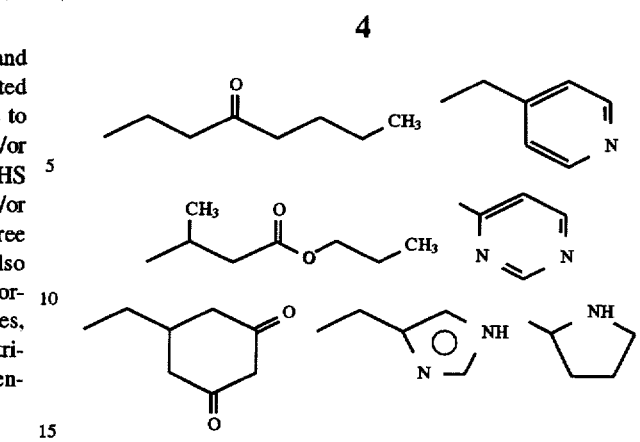

Preferred groups $E^1$ and $E^2$ are straight-chain alkyl radicals with up to 20 carbon atoms, hydrogen atoms, radicals of general formula IV

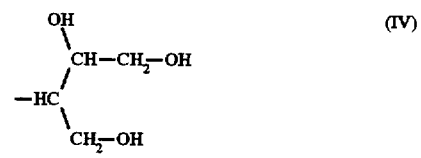

as well as radicals of the formulae

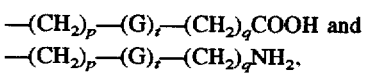

in which

G stands for oxygen or sulfur, p and q independently of one another, each stand for a number of from 1 to 18, t stands for 0 or 1, and $p+t+q \leq 20$, where the acid group can also be present as a salt of an inorganic or organic base, as an ester or as an amide, or the amino group can also be present as an ammonium salt with a physiologically compatible anion or as an amide.

As groups in which $E^1$ and $E^2$, together with inclusion of the nitrogen atom, form a five- to eight-membered, saturated or unsaturated heterocycle, there can be mentioned as examples the imidazolyl, pyrazolyl, pyrrolyl, 3-pyrrolinyl, pyrrolidinyl, morpholinyl group or the piperidinyl group.

As radicals Z, there can be mentioned as examples methyl, ethyl, n-propyl, i-propyl, n-butyl, i-butyl, pentyl, hexyl, cyclohexyl radicals or phenyl or benzyl radicals, as well as radicals of formulae:

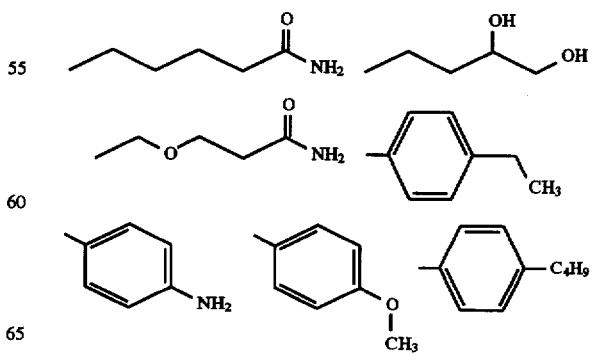

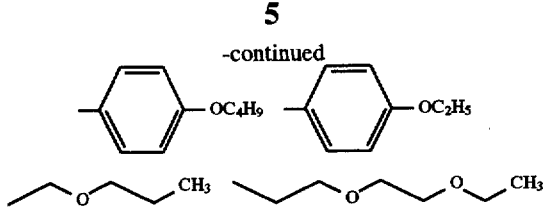

Radical Z can also contain, for example, a 3-indole radical and/or a histidine radical.

Preferred radicals Z are alkyl and cycloalkyl radicals, such as the methyl, ethyl, propyl, i-propyl, butyl, i-butyl, tert-butyl, pentyl, hexyl or cyclohexyl radical, as well as the phenyl and the benzyl radical.

Preferred radicals Z are, in addition, groups which are identical with radicals $Z^A$ occurring in the naturally occurring amino acids of general formula V.

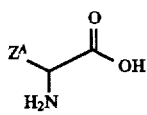

These $Z^A$ are:

| | |
|---|---|
| —H | Gly |
| —CH$_3$ | Ala |
| —CH(CH$_3$)$_2$ | Val |
| —CH$_2$—CH(CH$_3$)$_2$ | Leu |
| —CH$_2$—Ph | Phl |
| —CH$_2$OH | Ser |
| —CH(OH)—CH$_3$ | Thr |
| —CH$_2$SH | Cys |
| —CH$_2$—SCH$_3$ | Met |
| —CH$_2$CO$_2$H | Asp |
| —CH$_2$CH$_2$—CO$_2$H | Glu |
| —(CH$_2$)$_4$—NH$_2$ | Lys |

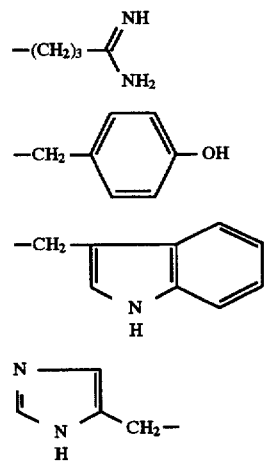

The HOOC, H$_2$N, HS or HO groups optionally present in Z can in this case be present in protected form. Details of protective group syntheses are further summarized below.

The linkage of compounds of general formula II with the amines of general formula III to obtain compounds of general formula Ia

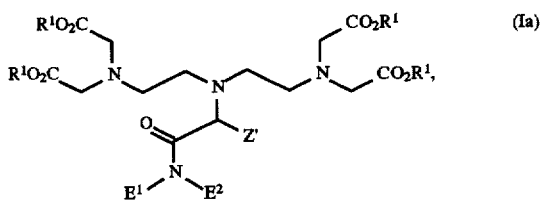

in which $E^1$, $E^2$, $R^1$ and Z' have the above-mentioned meanings, takes place in organic solvents such as toluene or tetrahydrofuran at temperatures preferably of about $-10°$ C. to $50°$ C., preferably at room temperature and below, more preferably with the addition of one or more activating reagents.

The activation to provide the activating reagent can take place, for example, by reaction of acid with dicyclohexylcarbodiimide, N-hydroxysuccinimide/dicyclohexylcarbodiimide, carbonyldiimidazole, 2-ethoxy-1-ethoxycarbonyl-1,2-dihydroquinoline, oxalic acid dichloride or isobutyl chloroformate in the way described in the literature:

Aktivierung von Carbonsäuren [Activation of Carboxylic Acids]. Übersicht in Houben-Weyl, Methoden der Organischen Chemie [Survey in Houben-Weyl, Methods of Organic Chemistry], Volume XV/2, Georg Thieme Verlag Stuttgart, 19.

Aktivierung mit Carbodiimiden [Activation with Carbodiimides]. R. Schwyzer and H. Kappeler, Helv. 46:1550 (1963).

E. Wünsch et al., B. 100:173 (1967). Aktivierung mit Carbodiimiden/Hydroxysuccinimid [Activation with Carbodiimides/Hydroxysuccinimide]: J. Am. Chem. Soc. 86:1839 (1964) as well as J. Org. Chem. 53:3583 (1988). Synthesis 453 (1972).

Anhydridmethode, 2-Ethoxy-1-ethoxycarbonyl-1,2-dihydrochinolin [Anhydride Methods, 2-Ethoxy-1-ethoxycarbonyl-1,2-dihydroquinoline]: B. Belleau et al., J. Am. Chem. Soc., 90:1651 (1986), H. Kunz et al., Int. J. Pept. Prot. Res., 26:493 (1985) and J. R. Voughn, Am. Soc. 73:3547 (1951).

Imidazolid-Methode [Imidazolide Methods]: B. F. Gisin, R. B. Menifield, D. C. Tosteon, Am. Soc. 91:2691 (1969).

Säurechlorid-Methoden, Thionylchlorid [Acid Chloride Methods, Thionyl Chloride]: Helv., 42:1653 (1959).

Oxalylchlorid [Oxalyl Chloride]: J. Org. Chem., 29:843 (1964).

The production of the complexing agents of general formula I takes place by subsequent mild cleavage of acid protective groups $R^1$ as well as of the protective groups, optionally contained in Z', from the compounds of general formula Ia

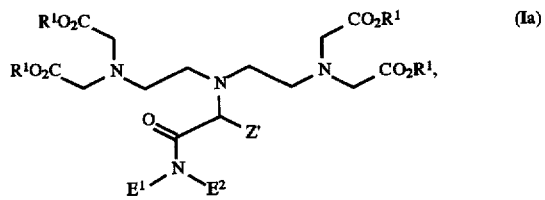

in which $E^1$, $E^2$, Z' and $R^1$ have the above-indicated meaning.

The cleavage of the protective groups takes place according to the processes known to one skilled in the art, for example by hydrolysis, hydroenolysis, alkaline saponification of esters with alkali in aqueous-alcoholic solution at temperatures of 0° to 50° C., acid saponification with mineral acids or in the case of tert-butyl esters with the help of trifluoroacetic acid. Preferred are the hydrogenolytic cleavage of the benzyl group and the saponification of the tert-butyl group with trifluoroacetic acid.

With respect to the prior art, the process according to the invention is distinguished by several decisive advantages:

1. The linkage of the amine of general formula III with the compounds of general formula II takes place selectively on the central carboxylic acid.
2. The linkage of the amine of general formula III with the compounds of general formula II takes place under very mild conditions. The temperature can be held below room temperature. As a result, undesirable secondary reactions, such as regroupings, racemizations, eliminations, etc. are suppressed. The method is therefore excellently suited for coupling to very sensitive amines.
3. The linkage of the amine of general formula III with the acid of general formula II in homogenous solution takes place with good solubility of all components in the solvent used.
4. The linkage of the amine of general formula III with the acid of general formula II can take place with the avoidance of chlorinated solvents, by which secondary reactions (such as, e.g., cleavage of HCl from the solvent) are avoided.
5. The acid protective groups in the compounds of general formula II are removed in a very mild way: existing amides are not saponified; regroupings, eliminations and racemizations do not take place.
6. The compounds of general formula I are obtained in high yield and purity.
7. The free acid of the compounds of general formula II can be activated in various ways and thus are reacted under optimum conditions with respect to the respective amine.

Production of the Starting Compounds

Numerous amines, which correspond to general formula III,

(III)

in which $E^1$ and $E^2$ have the above-mentioned meanings, can be purchased (e.g., E. Merck, Darmstadt, Fluka Chemie AG, CH-9470 Buchs) or can be produced as described, e.g., in Houben-Weyl, Methoden der organischen Chemie, Stickstoffverbindungen II [Nitrogen Compounds II], Volumes XI/1 and XI/2, Georg Thieme Verlag Stuttgart, 1957.

As amines of general formula III, there can be mentioned as examples ammonia, methylamine, dimethylamine, ethylamine, diethylamine, isopropylamine, diisopropylamine, cyclohexylamine, dicyclohexylamine, diisopropenylamine, cyclohexenylamine, 2-hydroxyethylamine, hex-5-enylamine, 2-ethylhexylamine, 2-ethoxyhexylamine, aniline, benzylamine, naphthylamine, piperidine, N-ethylpiperazine, 4-hydroxymethylpiperidine, 4-(2-hydroxyethyl)piperidine, 4-piperidone, piperidine-3-carboxylic acid diethylamide, 2,6-dimethylpiperidine, pyrazoline or oxazolidine.

The production of compounds of general formula II takes place in that a feedstock of general formula VI

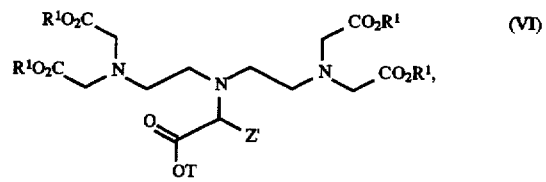

(VI)

in which $R^1$ and $Z'$ have the above-indicated meaning and T can be a straight-chain or branched $C_1$-$C_6$ alkyl group, a benzyl, trimethylsilyl, triisopropylsilyl, 2,2,2-trifluoroethoxy, 2,2,2-trichloroethoxy group, or a metal ion equivalent of an alkali or alkaline-earth element, in which T is always different from $R^1$, is converted by cleavage of group T to the compound of general formula II. Preferred radical T is the benzyl radical, if $R^1$ stands for a tert-butyl group.

The cleavage of protective group T from compounds of general formula VI takes place according to the processes known to one skilled in the art, such as, for example, by hydrolysis, hydrogenolysis, acid or alkaline saponification of esters in aqueous-alkaline medium, and optionally solubilizers, such as alcohols, preferably methanol, ethanol, isopropanol or ethers, such as tetrahydrofuran, 1,4-dioxane, 1,2-dimethoxyethane, can be added. As bases, alkali or alkaline-earth hydroxides or carbonates, such as, e.g., lithium hydroxide, sodium hydroxide, barium hydroxide or potassium carbonate and cesium carbonate can be used. Preferred temperatures are 0°–100° C., especially 0°–50° C. The subsequent isolation of the compound of general formula II takes place so that it is reacted with ammonium salts, such as, e.g., $NH_4Cl$, $(NH_4)_2SO_4$ or $(NH_4)_3PO_4$, or the salts are converted to free acids with acid ion exchanger.

Also, the use of diluted citric or acid ion exchanger has proven itself for the release of the acid group from the alkali or alkaline-earth salts.

The acid saponification is performed with mineral acids, such as, e.g., hydrochloric acid, sulfuric acid or else also organic acids (e.g., trifluoroacetic acid) at temperatures of 0°–100° C., preferably 0°–50° C., in the case of trifluoroacetic acid between 0°–25° C. The cleavage of silyl-containing protective groups takes place with fluoride ions.

The hydrogenolytic cleavage of benzyl derivatives takes place with use of the palladium catalysts known to one skilled in the art, preferably 10% palladium on activated carbon or Pearlman's catalyst $Pd(OH)_2$ on carbon. Homogeneous catalysts of the Wilkinson catalyst type can also be used. The hydrogenation is performed in alcohols such as methanol, ethanol or isopropanol, but preferably isopropanol at temperatures between 10°–50° C., but preferably at room temperature and normal pressure.

The production of compounds of general formula VI takes place, for example, in that an amino acid derivative of general formula VII

(VII)

in which T and $Z'$ have the above-indicated meaning, is reacted with an alkylating agent of general formula VIII

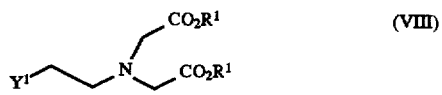

(VIII)

in which
$R^1$ has the above-indicated meaning and
$Y^1$ stands for a halogen atom, such as Cl, Br or I, but preferably Cl (see also M. A. Williams, H. Rapoport, J. Org. Chem., 58, 1151 (1993)).

Preferred amino acid derivatives are the esters of naturally occurring α-amino acids.

The reaction of compound (VII) with compound (VIII) takes place preferably in a buffered alkylation reaction, in which an aqueous phosphate buffer solution is used as buffer. The reaction takes place at pH 7–9, but preferably at pH 8. The buffer concentration can be between 0.1–2.5M, but a 2M phosphate-buffer solution preferably is used. The temperature of the alkylation can be between 0° and 50° C., the preferred temperature is room temperature.

The reaction is performed in a polar solvent, such as, e.g., acetonitrile, tetrahydrofuran, 1,4-dioxane or 1,2-dimethoxyethane. Acetonitrile is preferably used.

If $Y^1$ in general formula VIII is a Cl or Br atom, an alkali iodide, such as, e.g., NaI, KI, can be added to the reaction in catalytic amounts. The amino acid esters of general formula VII used in the reaction can be produced from the commercially available amino acids according to methods known to one skilled in the art (e.g.: Houben-Weyl. Methoden der organischen Chemie, Synthese von Peptiden [Synthesis of Peptides], Part II, Volume XV/2, Georg Thieme Verlag Stuttgart, 1974, p. 3 ff). As commercially available products, amino acids and derivatives can be obtained, e.g., from Fluka Chemie [Fluka Chemistry]AG, CH-9470 Buchs or the BACHEM Feinchemikalien [BACHEM Fine Chemicals]AG, CH-4416 Bubendorf.

Preferred amino acid derivatives of general formula VII are the amino acid benzyl esters. In the synthesis of these compounds, salts (such as, e.g., hydrochlorides, hydrosulfates, sulfates, phosphates or p-toluene sulfonates) generally accumulate, which can be used advantageously directly in the reaction.

The structural element of general formula VIII used in the alkylation can be produced according to the description of Rapoport if $Y^1$=Br. But the corresponding compound with $Y^1$=Cl can be used in the same way for the above-described reaction. The chlorine compound can be produced economically, moreover, from the alcohol of general formula IX, in which $R^1$ represents the benzyl or tert-butyl group,

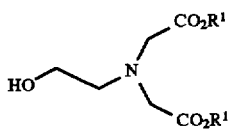 (IX)

by reaction with thionyl chloride.

An alternative method for the production of compounds of general formula VI consists in that a compound of general formula X

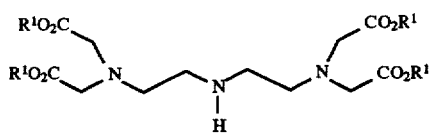 (X)

with
$R^1$ in the above-indicated meaning is reacted with an alkylating agent of general formula XI

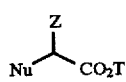 (XI)

in which
T and Z have the above-mentioned meaning and in which Nu stands for a nucleofuge, such as Cl, Br, I, p-$CH_3C_6H_4SO_3$, $CH_3SO_3$ or $CF_3SO_3$, preferably for Br and Cl.

The reaction to the compound of general formula VI takes place in polar solvents, such as dimethylformamide, acetonitrile, tetrahydrofuran, 1,4-dioxane, formamide, dimethylacetamide, dimethyl sulfoxide, acetone, as well as in alcohols, such as, for example, methanol, ethanol, isopropanol, preferably in acetonitrile and dimethylformamide. In the case of the preferred bromides and chlorides, catalytic amounts of iodide can be added. For catching the acid that has developed in the alkylation, organic bases, such as, e.g., triethylamine, Hünig base or 1,4-diazabicyclooctane (DABCO), or else metal hydrides, for example sodium hydride or alkali or alkaline-earth hydroxides or their carbonates, are used. Preferably potassium carbonate is used. The reactions take place at 0°–100°, preferably between 20° and 60° C. The alkylating reagents described by general formula XI are partially commercially available or can be produced from the corresponding carboxylic acids, or α-hydroxycarboxylic acids in a way known in the literature (see, for example: C. F. Ward, Soc., 121:1164 (1922)).

The compound of general formula X is obtained by cleavage of protective group A from the compound of general formula XII

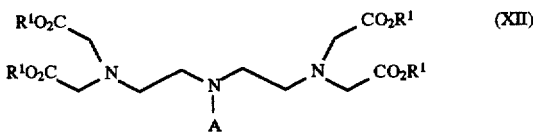 (XII)

in which
$R^1$ has the above-mentioned meaning and
A stands for a protective group, such as, for example, a benzyloxycarbonyl, tert-butyloxycarbonyl (BOC), fluorenylmethoxycarbonyl (FMOC), benzyl, 4-methoxybenzyl, $(CH_3)_3Si$—$(CH_2)_2$—$SO_2$, $CF_3CO$, $Cl_3CCO$, $(C_6H_5)$(tert-Bu)$_2$Si or a trityl group.

The cleavage takes place, if A is the BOC radical, by treatment with trifluoroacetic acid. Silyl protective groups are cleaved with diluted mineral acid or with fluoride ions. If A means the $(CH_3)_3Si$—$(CH_2)_2$—$SO_2$ group, tetrabutylammonium fluoride is used as cleavage reagent. If A represents the benzyl radical or the benzyloxycarbonyl radical, the latter is cleaved by hydrogenolysis with palladium catalyst (10% Pd/C) or more advantageously with Pearlman's catalyst (Pd(OH)$_2$/C) in alcohol, preferably ethanol, at room temperature.

The compound of general formula XII is obtained from the compound of general formula XIII

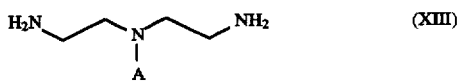 (XIII)

in which
A has the above-mentioned meaning, by reaction with α-haloacetic acid esters.

The compound of general formula XII, in which A represents the benzyl radical, can also be produced by reaction of benzylamine with the alkylating reagent of general formula VIII, as described above for the amino acid esters of general formula VII.

Preferably the chloro- or bromoacetic acid-tert-butyl esters as well as the corresponding benzyl esters are used. The reaction is conducted analogously to that described in detail for the reaction of the compound of general formula VII with the compound of the general formula VIII to obtain the compound of formula VI.

The compound of general formula XIII is produced by a cleavage of protective group L, known to one skilled in the art, from the compound of general formula XIV

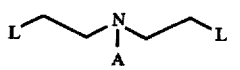  (XIV)

in which

A has the above-mentioned meaning and in which

L stands for a group -NHD, in which

D represents, e.g., the benzyloxycarbonyl, BOC, $CF_3CO$, $Cl_3CCO$ or the trityl group or L stands for a phthalimido group.

If D stands for the benzyloxycarbonyl group, a hydrogenolysis takes place in the presence of palladium catalysts, as described above.

If D is the $CF_3CO$ group, a saponification with alkali or alkaline-earth hydroxides or their carbonates, but preferably potassium carbonate, is performed. Ammonia water can also be used. As solvent, preferably mixtures of alcohols or tetrahydrofuran or 1,4-dioxane with water are used. The reaction temperatures are between 0°–60° C., the reaction is preferably performed at room temperature. If L is the phthalimino group, the cleavage of the phthalyl protective group takes place by hydrazinolysis or by treatment with alkali hydroxides, preferably sodium hydroxide or potassium hydroxide in aqueous alcohols, preferably n-butanol with refluxing or by treatment with aqueous mineral acids, preferably concentrated hydrochloric acid, with refluxing.

It has proven especially advantageous to undertake the saponification with aqueous potassium carbonate solution, since in this way, the alkylation to tetraesters of general formula XII can be undertaken without isolating the intermediate stage of general formula XIII.

1,4,7-Triaza-4-benzyl-heptane can also be produced as described in EP 0292689.

The compound of general formula XIV can be obtained by reaction of the compound of general formula XV

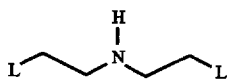  (XV)

in which

L stands for group -NHD, with D having the above-indicated meaning, or for a phthalimido group, with the standard protective group reagents (see, e.g., Protective Groups in Organic Syntheses, Second Edition, T. W. Greene and P. G. M. Wuts, John Wiley & Sons, Inc., New York, 1991).

The compounds of general formula XV are obtained by reaction of an acylating reagent of general formula XVI

 D—G  (XVI)

with diethylenetriamine (XVII)

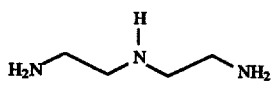  (XVII)

in which

G stands for a C≡N group or an $OR^3$ group, $R^3$ stands for a branched or unbranched, completely or partially fluorinated $C_1$–$C_6$ alkyl group or a benzyl group, or if L represents the phthalimino group, D—G stands for phthalic anhydride.

In addition to the mentioned phthalic anhydride, preferred reagents D—G are trifluoroacetic acid ethyl ester and cyanobenzyl formate.

Thus, the reaction of diethylenetriamine (XVII) with trifluoroacetic acid ethyl ester in ethanol at room temperature yields, in almost quantitative yield, the already known (U.S. Pat. No. 4,415,737 A (1983)) 1,7-bis-trifluoroacyl derivative (see Examples).

The 1,7-dibenzyloxycarbonyl compound (see Examples) can be obtained by reaction of triamine (XVII) with cyanobenzyl formate in tetrahydrofuran (Shun-Ichi Munehashi et al., Chemistry Letters, pp. 879–882 (1987)).

The phthalimido protective group can, as described in J. Org. Chem. USSR, 23:3302 (1987), be introduced into diethylenetriamine (XVII).

Protective Groups

The protection of the designated groups in radicals $E^1$, $E^2$ and Z can take place with numerous possibilities known to one skilled in the art. The embodiments described below are used in explanation of these protective group techniques without being limited to these synthesis methods.

As acid protective groups, $C_1$–$C_6$ alkyl, $C_6$–$C_{10}$ aryl and $C_{6-C10}$-Ar($C_{1-C4}$) alkyl groups as well as trialkylsilyl groups are suitable. Preferred are the methyl, ethyl, propyl, isopropyl, n-butyl, i-butyl and the tert-butyl group.

The cleavage of these acid protective groups takes place according to the processes known to one skilled in the art, for example by hydrolysis, hydrogenolysis, alkaline saponification of esters with alkali in aqueous-alcoholic solution at temperatures of 0° to 50° C., acid saponification with mineral acids or in the case of tert-butyl esters with the help of trifluoroacetic acid.

As hydroxy protective groups, e.g., the benzyl, 4-methoxybenzyl, 4-nitrobenzyl, trityl, diphenylmethyl, trimethylsilyl, dimethyl-tert-butylsilyl, diphenyl-tert-butylsilyl groups are suitable.

The hydroxy groups can also be present e.g., as THP-ethers, α-alkoxyethylethers, MEM ethers or as esters with aromatic or aliphatic carboxylic acids, such as, e.g., acetic acid or benzoic acid. In the case of polyols, the hydroxy groups can also be protected in the form of ketals with, e.g., acetone, acetaldehyde, cyclohexanone or benzaldehyde.

The hydroxy protective groups can be released according to the methods in literature known to one skilled in the art, e.g., by hydrogenolysis, acid treatment of the ethers and ketals or alkali treatment of esters (see, e.g., Protective Groups in Organic Syntheses, Second Edition, T. W. Greene and P. G. M. Wuts, John Wiley & Sons, Inc., New York, 1991).

The thiol groups can be protected as benzyl ethers, which can be cleaved with sodium in ammonia or boiling ethanol (W. I. Patterson, v. du Vigneaud, J. Biol. Chem. 111:393, 1993). S-tert-butyl ethers are readily cleavable with hydrogen fluoride/anisole at room temperature (S. Salzakibona et al., Bull. Chem. Soc. Japn., 40:2164, (1967)). S-Benzyloxycarbonyl derivatives can be easily cleaved by concentrated ammonia at room temperature (A. Berger et al., J. Am. Chem. Soc., 78:4483, 1956). Only at boiling temperature are S-benzyloxycarbonyl derivatives cleaved from trifluoroacetic acid (L. Zervas et al., J. Am. Chem. Soc., 85:1337 (1963)).

The $NH_2$ groups can be protected in varied ways and again opened. The N-trifluoroacetyl derivative is cleaved by potassium or sodium carbonate in water (H. Newman, J. Org. Chem., 30:287 (1965), M. A. Schwartz et al., J. Am. Chem. Soc., 95, G12 (1973)) or simply by ammonia (M. Imazama and F. Eckstein, J. Org. Chem., 44:2039 (1979)). The tert-butyloxycarbonyl derivative is equally easy to cleave: stirring with trifluoroacetic acid is sufficient (B. F. Lundt et al., J. Org. Chem., 43:2285 (1978)).

The group of the $NH_2$ protective groups to be cleaved hydrogenolytically or reductively is very large: the N-benzyl group can be cleaved easily with hydrogen/Pd-C (W. H.

Hartung and R. Simonoff, Org. Reactions VII, 263 (1953)), which also applies for the trityl group (L. Zervas et al., J. Am. Chem. Soc., 78:1359 (1956)) and the benzyloxycarbonyl group (M. Bergmann and L. Zervas, Ber. 65:1192 (1932)).

Of the silyl derivatives, the easily cleavable tert-butyldiphenylsilyl compounds (L. E. Overman et al., Tetrahedron Lett. 27:4391 (1986)), as also the 2-(trimethylsilyl)-ethyl carbamates (L. Grehn et al., Angew. Chem. [Applied Chemistry] Int. Ed. Engl., 23:296 (1983)) and the 2-trimethylsilylethanesulfonamides (R. S. Garigipati and S. M. Weinreb, J. Org. Chem., 53:4143 (1988)) are used, which can be cleaved with fluoride ions.

Especially easily cleavable is the 9-fluorenylmethylcarbamate: the cleavage takes place with amines, such as piperidine, morpholine, 4-dimethylaminopyridine, but also with tetrabutylammonium fluoride (L. A. Corpino et al., J. Org. Chem., 55:1673 (1990), M. Ueki and M. Amemiya, Tetrahedron Lett., 28:6617 (1987)).

Use of the Process Products

The complexing agents of general formula I produced according to the process of the invention can be used:

1. as antidote for detoxification in the case of inadvertent incorporation of heavy metals and/or their radioactive isotopes in the form of free complexing agents and/or salts of complexing agents with physiologically compatible cations.
2. for NMR diagnosis in the form of their complexes with divalent and trivalent ions of the elements of atomic numbers 21–29, 42, 44 and 57–70. Suitable ions are, for example, the chromium(III), manganese(II), iron(II), cobalt(II), nickel(II), copper(II), praseodymium(III), neodymium(III), samarium(III) and ytterbium(III) ion. Because of their very strong magnetic moment, the gadolinium(III), terbium(III), dysprosium(III), holmium (III), erbium(III) and iron(III) ions are especially preferred.
3. for diagnostic radiology in the form of complexes of an element of a higher atomic number, which assures a sufficient absorption of x rays. It has been found that complexes according to the invention, which as the central atom contain elements of atomic numbers 57–83, are suitable for this application.
4. for radiodiagnosis and radiotherapy in the form of their complexes of radioactive central ions. Suitable are, for example, radioisotopes of the elements copper, cobalt, germanium, yttrium, strontium, ytterbium, gadolinium, samarium and iridium.

The production of complexes for the production of NMR or x-ray diagnostic agents can take place in the way in which it was disclosed in patent specifications EP 71564, EP 130934 and DE-OS 3401052. In this respect, the metal oxide or a metal salt (for example, a chloride, nitrate, acetate, carbonate or sulfate) of the element of atomic numbers 21–29, 32, 39, 42, 44 or 57–83 is dissolved or suspended in water and/or a lower alcohol (such as methanol, ethanol or isopropanol) and reacted with the solution or suspension of the equivalent amount of the complexing agent of general formula I according to the invention. If desired, still present acid hydrogen atoms of the acid groups can be substituted by cations of inorganic and/or organic bases or amino acids.

The neutralization takes place in this case with the help of inorganic bases (e.g., hydroxides, carbonates or bicarbonates) of, e.g., sodium, potassium or lithium and/or organic bases, such as, i.a., primary, secondary and tertiary amines, such as, e.g., ethanolamine, glucamine, N-methylglucamine and N,N-dimethylglucamine, as well as basic amino acids, such as, e.g., lysine, arginine and ornithine.

If the complexing agents are to be used for the production of radiodiagnostic agents or radiotherapeutic agents, the production of complexes from the complexing agents can take place according to the methods described in "Radiotracers for Medical Applications," Vol. I, CRC Press, Boca Raton, Florida.

The production of pharmaceutical agents from the complexes takes place in a way known in the art, by the complexes—optionally by adding the additives usual in galenicals—being suspended or dissolved in aqueous medium and then the suspension or solution optionally being sterilized. Suitable additives are, for example, physiologically harmless buffers (such as, for example, tromethamine), small additions of complexing agents (such as, for example, DTPA or the respective compounds of general formula I according to the invention) and/or their calcium, magnesium or zinc complexes or optionally electrolytes (such as, for example, sodium chloride) as well as antioxidants (such as, for example, ascorbic acid).

If suspensions or solutions of the agents according to the invention in water or physiological salt solution are desired for enteral administration or other purposes, they are mixed with one or more adjuvants usual in galenicals, such as, for example, methylcellulose, lactose or mannitol, and/or surfactants, such as, for example, lecithins, Tween® or Myrj®, and/or flavoring substances for taste correction, such as, for example, ethereal oils.

It is also possible, in principle, to produce the pharmaceutical agents according to the invention even without isolating the complex salts. In each case, special care must be used to undertake the chelation, so that the salts and salt solutions according to the invention are practically free of noncomplexed metal ions having a toxic effect.

In general, it has been possible to provide a process which makes possible the synthesis of new complexing agents, which open up new possibilities in diagnostic and therapeutic medicine.

In the foregoing and in the following examples, all temperatures are set forth uncorrected in degrees Celsius; and, unless otherwise indicated, all parts and percentages are be weight.

The entire disclosure of all applications, patents and publications, cited above and below, including German Patent Application No. 195 07 821.7,is hereby incorporated by reference.

The following examples are used for a more detailed explanation of the object of the invention without intending to be limited to this object.

EXAMPLES

Example 1

3,9-Bis(tert-butoxycarbonylmethyl)-3,6,9-triazaundecanedioic acid-di-tert-butyl ester a) 1,7-Bis(trifluoroacetyl)-1,4,7-triazaheptane 113.3 g (790 mmol) of trifluoroacetic acid ethyl ester is instilled in a solution of 41.14 g (390 mmol) of 1,4,7-triazaheptane in 350 ml of tetrahydrofuran at 0° C. and under nitrogen. It is allowed to stir overnight at room temperature, concentrated by evaporation in a vacuum. The remaining oil is crystallized from hexane.

Yield: 115 g (99.9% of theory)

Melting point: 68°–70° C.

Elementary analysis: Cld: C 32.55 H 3.76 F 38.62 N 14.24
Fnd: C 32.63 H 3.75 F 38.38 N 14.19 b) 1,7-Bis(trifluoroacetyl)-4-benzyloxycarbonyl-1,4,7-triazaheptane 14.75 g (50 mmol) of the trifluoroacetyl compound produced under Example 1a) as well as 8.3 ml (60 mmol) of triethylamine are dissolved in 120 ml of dichloromethane and cooled to 0° C. 7.5 ml (53 mmol) of benzyl chloroformate (97%), dissolved in 20 ml of dichloromethane, is now instilled with stirring. It is allowed to stir overnight at room temperature, the salts are extracted with distilled water, the dichloromethane solution is dried on sodium sulfate, evaporated to dryness in a vacuum and the residue is crystallized from ether/hexane.

Yield: 18.40 g (85.7% of theory)
Melting point: 131°–32° C.
Elementary analysis: Cld: C 44.76 H 3.99 F 26.55 N 9.79 Fnd: C 44.87 H 4.03 F 26.62 N 9.61 c) 3,9-Bis(tert-butoxycarbonylmethyl)-6-benzyloxycarbonyl-3,6,9-triazaundecanedicarboxylic acid-di-tert-butyl ester 4.29 g (10 mmol) of the trifluoroacetyl derivative produced under Example 1b) is dissolved in 30 ml of ethanol and mixed with 800 mg (20 mmol) of sodium hydroxide solution in 10 ml of distilled water. It is stirred for 3 hours at room temperature, evaporated to dryness in a vacuum at 40° C. bath temperature, water residues are removed by azeotropic distillation with isopropanol and taken up in 30 ml of dimethylformamide. Then, 6.9 g (50 mmol) of potassium carbonate as well as 9.7 g (50 mmol) of bromoacetic acid-tert-butyl ester are added to it and the 4-benzyloxycarbonyl-1,4,7-triazaheptane is alkylated at room temperature overnight. The dimethylformamide is then drawn off in an oil pump vacuum, the residue is dispersed between water and dichloromethane, the organic solution is dried on sodium sulfate, evaporated to dryness in a vacuum and the residue is purified by chromatography on silica gel. The title compound is eluted with ethyl acetate/hexane. It is obtained as foam.

Yield: 6.49 g (93.6% of theory)
Elementary analysis: Cld: C 62.32 H 8.57 N 6.06 Fnd: C 62.41 H 8.66 N 6.01 d) 3,9-Bis(tert-butoxycarbonylmethyl)-3,6,9-triazaundecanedicarboxylic acid-di-tert-butyl ester 3.5 g (5 mmol) of the compound produced under Example 1c) is dissolved in 100 ml of ethanol, mixed with 200 mg of Pearlman's catalyst (Pd 20% on activated carbon) and hydrogenated until the calculated amount of hydrogen is taken up. It is suctioned off from the catalyst and evaporated to dryness in a vacuum. The title compound is obtained as white foam.

Yield: 2.80 g (99.9% of theory)
Elementary analysis: Cld: C 60.08 H 9.54 N 7.51 Fnd: C 60.02 H 9.62 N 7.56 e) 3,9-Bis(tert-butoxycarbonylmethyl)-6-(2-methyl)-ethoxycarbonylmethyl-3,6,9-triazaundecanedioic acid-di-tert-butyl ester 5.60 g (10 mmol) of the amino compound produced under Example 1d) is dissolved in 30 ml of dimethylformamide. Then, 1.66 g (12 mmol) of potassium carbonate as well as 2.17 g (12 mmol) of 2-bromopropionic acid ethyl ester are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 4.18 g (63.4% of theory)
Elementary analysis: Cld: C 60.07 H 9.32 N 6.37 Fnd: C 60.18 H 9.40 N 6.31 f) 3,9-Bis(tert-butoxycarbonylmethyl)-6-(2-methyl)-carboxymethyl-3,6,9-triazaundecanedioic acid-di-tert-butyl ester 6.60 g (10 mmol) of the compound produced under Example 1e) is dissolved in 50 ml of ethanol. The solution of 400 mg (10 mmol) of sodium hydroxide in 5 ml of distilled water is then added to it and stirred for 3 hours at 50° C. According to the thin-layer chromatogram, saponification is quantitative. It is evaporated to dryness in a vacuum, traces of water are removed by codistillation with ethanol and the residue is dried at 40° C. in a vacuum. The title compound is obtained as white powder. The remaining white residue is dissolved in 80 ml of wet ethanol (9:1) and mixed with stirring with the solution of 535 mg (10 mmol) of ammonium chloride in 10 ml of distilled water. It is evaporated to dryness in a vacuum, the soluble portions are taken up in butanol and evaporated to dryness again in a vacuum. The residue is extracted with toluene. The organic solution is evaporated to dryness in a vacuum and the title compound is obtained as foam.

Yield: 5.35 g (84.7% of theory)
Elementary analysis: Cld: C 58.93 H 9.09 N 6.65 Fnd: C 59.01 H 9.16 N 6.60 g) 3,9-Bis(tert-butoxycarbonylmethyl)-6-(2-methyl)-decylaminocarbonylmethyl-3,6,9-triazaundecanedioic acid-di-tert-butyl ester 5.00 g (7.91 mmol) of the title compound of Example 1f) is dissolved in 25 ml of dimethylformamide, and 1.00 g (8.70 mol) of N-hydroxysuccinimide is added. It is cooled off to 0° C. and 1.795 g (8.7 mmol) of dicyclohexylcarbodiimide is added. It is stirred for one hour at 0° C. and then for 4 hours at room temperature. It is cooled off to 0° C. and a solution of 1.25 g of decylamine (7.91 mmol) in 10 ml of dimethylformamide is instilled within 10 minutes. It is stirred for one hour at 0° C., then overnight at room temperature. It is evaporated to dryness in a vacuum and the residue is taken up in 100 ml of ethyl acetate. It is filtered off from precipitated urea and the filtrate is washed twice with 100 ml each of 5% aqueous soda solution. The organic phase is dried on magnesium sulfate and evaporated to dryness in a vacuum. The residue is chromatographed on silica gel (mobile solvent: n-hexane/ethyl acetate 20:1). 5.31 g (87% of theory) of a colorless oil is obtained.

Elementary analysis: Cld: C 63.86 H 10.20 N 7.27 Fnd: C 63.95 H 10.28 N 7.18 h) 3,9-Bis(carboxymethyl)-6-(2-methyl)-decylaminocarbonyl-methyl-3,6,9-triazaundecanedioic acid 5 g (6.48 mmol) of the title compound of Example 1g) is dissolved in 100 ml of trifluoroacetic acid. It is stirred overnight at room temperature. It is evaporated to dryness in a vacuum and the residue is chromatographed on silica gel (mobile solvent: ethanol/25% ammonia water 20:1). The fractions containing the product are evaporated to dryness in a vacuum. The residue is dissolved in 100 ml of water. 20 ml of acid ion exchanger IR 120 ($H^+$ form) is added and stirred for 10 minutes at room temperature. It is filtered off from the ion exchanger and evaporated to dryness in a vacuum.

Yield: 2.34 g (61% of theory) of a vitreous solid
Water content: 7.5%
Elementary analysis: Cld: C 54.93 H 8.48 N 10.25 Fnd: C 54.85 H 8.55 N 10.17

Example 2

3,9-Bis(tert-butoxycarbonylmethyl)-6-(2-benzyl)-carboxymethyl-3,6,9-triazaundecanedioic acid-di-tert-butyl ester a) 1,7-Bis(benzyloxycarbonyl)-4,7-triazaheptane 4.87 g (47.2 mmol) of 1,4,7-triazaheptane as well as 5 ml of triethylamine are dissolved in 100 ml of dichloroethane. The solution of 15.22 g (94.4 mmol) of cyanobenzyl formate in 200 ml of dichloromethane is instilled in this solution within 3 hours. It is allowed to stir for 2 more days at room temperature, then evaporated to dryness in a vacuum, taken up in diethyl ether and washed with sodium bicarbonate solution. The ether solution is dried on sodium sulfate and evaporated to dryness in a vacuum. The residue is crystallized from a little ethanol. The title compound crystallizes into white needles.

Yield: 11.46 g (65.7% of theory)
Melting point: 73°–75° C.
Elementary analysis: Cld: C 64.67 H 6.78 N 11.31 Fnd: C 64.82 H 6.64 N 11.28 b) 1,7-Bis(benzyloxycarbonyl)-4-trifluoroacetyl-1,4,7-triazaheptane Analogously to Example 1a), 37.14 g (100 mmol) of the amino compound produced under Example 2a is reacted with 15.63 g (110 mmol) of trifluoroacetic acid ethyl ester in 100 ml of tetrahydrofuran and worked up. The title compound is obtained as oil.

Yield: 43.57 g (93.2% of theory)
Elementary analysis: Cld: C 56.53 H 5.18 F 12.19 N 8.99 Fnd: C 56.60 H 5.24 F 12.14 N 9.04 c) 3,9-Bis(tert-butoxycarbonylmethyl)-6-trifluoroacetyl-3,6,9-triazaundecanedioic acid-di-tert-butyl ester Analogously to Example 1d), 4.675 g (10 mmol) of the trifluoroacetyl compound, produced under Example 5f), in 100 ml of ethanol is hydrogenated with 0.5 g of Pearlman's catalyst (Pd 20%, C) to 4-trifluoroacetyl-1,4,7-triazaheptane and worked up. The amino compound is then alkylated according to Example 1e) in 30 ml of dimethylformamide with 9.7 g (50 mmol) of bromoacetic acid-tert-butyl ester in the presence of 6.9 g (50 mmol) of potassium carbonate. The working-up and purification of the title compound also takes place analogously to 5c).

Yield: 5.88 g (89.6% of theory)
Elementary analysis: Cld: C 54.95 H 7.99 F 8.69 N 6.41 Fnd: C 54.90 H 8.05 F 8.62 N 6.36 d) 3,9-Bis(tert-butoxycarbonylmethyl)-3,6,9-triazaundecanedicarboxylic acid-di-tert-butyl ester Analogously to Example 1c), 6.57 g (10 mmol) of the trifluoroacetyl compound, produced under Example 2c), is dissolved in 50 ml of ethanol and saponified with 400 mg (10 mmol) of sodium hydroxide solution. It is concentrated by evaporation, the amino compound is taken up in warm toluene, washed with a little water, dried on sodium sulfate and evaporated to dryness in a vacuum. The title compound is obtained as foam.

Yield: 5.24 g (93.6% of theory)
Elementary analysis (relative to anhydrous substance): Cld: C 60.08 H 9.54 N 7.51 Fnd: C 60.02 H 9.48 N 7.44 e) 3,9-Bis(tert-butoxycarbonylmethyl)-6-(2-benzyl)-ethoxycarbonylmethyl-3,6,9-triazaundecanedioic acid-di-tert-butyl ester 5.60 g (10 mmol) of the amino compound produced under Example 2d) is dissolved in 30 ml of dimethylformamide. Then, 1.66 g (12 mmol) of potassium carbonate as well as 3.0 g (12 mmol) of 2-bromophenylpropionic acid ethyl ester are added to it at room temperature and stirred overnight. It is then poured on ice water, extracted with ethyl acetate, the organic solution is dried on sodium sulfate, evaporated to dryness in a vacuum, and the title compound is obtained by chromatography on silica gel. A mixture of ethyl acetate/hexane is used as eluant.

Yield: 4.30 g (58.4% of theory)
Elementary analysis: Cld: C 64.65 H 9.00 N 5.95 Fnd: C 64.62 H 9.07 N 5.90 f) 3,9-Bis(tert-butoxycarbonylmethyl)-6-(2-benzyl)-carboxymethyl-3,6,9-triazaundecanedioic acid-di-tert-butyl ester 7.06 g (10 mmol) of the compound produced under Example 2e) is dissolved in 50 ml of ethanol. The solution of 400 mg (10 mmol) of sodium hydroxide in 5 ml of distilled water is then added to it and stirred for 3 hours at 50° C. According to the thin-layer chromatogram, saponification is quantitative. It is evaporated to dryness in a vacuum, traces of water are removed by codistillation with ethanol and the residue is dried at 40° C. in a vacuum. The title compound is obtained as white powder. The remaining white residue is dissolved in 80 ml of wet ethanol (9:1) and mixed with stirring with the solution of 535 mg (10 mmol) of ammonium chloride in 10 ml of distilled water. It is evaporated to dryness in a vacuum, the soluble portions are taken up in butanol and evaporated to dryness again in a vacuum. The residue is extracted with toluene. The organic solution is evaporated to dryness in a vacuum and the title compound is obtained as foam.

Yield: 6.03 g (85.2% of theory)
Elementary analysis: Cld: C 63.79 H 8.77 N 6.20 Fnd: C 63.68 H 8.83 N 6.26 g) 3,9-Bis(tert-butoxycarbonylmethyl)-6-(2-benzyl)-pentylaminocarbonylmethyl-3,6,9-triazaundecanedioic acid-di-tert-butyl ester 5.00 g (7.91 mmol) of the title compound of Example 2f) is dissolved in 25 ml of dimethylformamide, and 894 mg (7.77 mol) of N-hydroxysuccinimide is added. It is cooled off to 0° C. and 1.603 g (7.77 mmol) of dicyclohexylcarbodiimide is added. It is stirred for one hour at 0° C and then for 4 hours at room temperature. It is cooled off to 0° C. and a solution of 0.62 g of pentylamine (7.06 mmol) in 10 ml of dimethylformamide is instilled within 10 minutes. It is stirred for one hour at 0° C., then overnight at room temperature. It is evaporated to dryness in a vacuum and the residue is taken up in 100 ml of ethyl acetate. It is filtered off from precipitated urea and the filtrate is washed twice with 100 ml each of 5% aqueous soda solution. The organic phase is dried on magnesium sulfate and evaporated to dryness in a vacuum. The residue is chromatographed on silica gel (mobile solvent: n-hexane/ethyl acetate 20:1). 4.77 g (87% of theory) of a colorless oil is obtained.

Elementary analysis: Cld: C 64.92 H 9.34 N 7.21 Fnd: C 64.81 H 9.28 N 7.25 h) 3,9-Bis(carboxymethyl)-6-(2-benzyl)-pentylaminocarbonylmethyl-3,6,9-triazaundecanedioic acid 4.50 g (5.79 mmol) of the title compound of Example 2g) is dissolved in 100 ml of trifluoroacetic acid. It is stirred overnight at room temperature. It is evaporated to dryness in a vacuum and the residue is chromatographed on silica gel (mobile solvent: ethanol/25% ammonia water 20:1). The fractions containing the product are evaporated to dryness in a vacuum. The residue is dissolved in 100 ml of water. 20 ml of acid ion exchanger IR 120 (H$^+$ form) is added and stirred for 10 minutes at room temperature. It is filtered off from the ion exchanger and evaporated to dryness in a vacuum.

Yield: 2.28 g (67% of theory) of a vitreous solid
Water content: 6.1%
Elementary analysis (relative to anhydrous substance): Cld: C 56.51 H 7.30 N 10.14 Fnd: C 56.61 H 7.22 N 10.03

Example 3

3,9-Bis(tert-butoxycarbonylmethyl)-6-(2-isopropyl)-carboxymethyl-3,6,9-triazaundecanedioic acid-di-tert-butyl ester a) 1,7-Bis(trifluoroacetyl)-4-benzyl-1,4,7-triazaheptane 29.52 g (100 mmol) of the bis(trifluoroacetyl) compound produced under Example 1a) is dissolved in 200 ml of dimethylformamide. Then, 16.6 g (120 mmol) of potassium carbonate as well as 20.53 g (120 mmol) of benzyl bromide are added to it at room temperature and stirred overnight. Then, it is diluted with 500 ml of diethyl ether, suctioned off from the salts, the ether is drawn off in a vacuum and then concentrated by evaporation to 50 ml in an oil pump vacuum. It is diluted with 600 ml of diethyl ether, poured on ice water and the organic solution is taken up, dried on sodium sulfate, evaporated to dryness in a vacuum and the title compound is obtained by chromatography on silica gel. A mixture of ethyl acetate/hexane is used as eluant.

Yield: 317.50 g (82.4% of theory)

Elementary analysis: Cld: C 46.76 H 4.45 F 29.58 N 10.91 Fnd: C 46.83 H 4.51 F 29.50 N 10.87 b) 3,9-Bis(tert-butoxycarbonylmethyl)-6-benzyl-3,6,9-triazaundecanedicarboxylic acid-di-tert-butyl ester 38.53 g (100 mmol) of the trifluoroacetyl derivative produced under 3a) is dissolved in 300 ml of ethanol and mixed with 8 g (200 mmol) of sodium hydroxide solution in 100 ml of distilled water. It is stirred for 3 hours at room temperature, evaporated to dryness in a vacuum at 50° C. bath temperature, water residues are removed by azeotropic distillation with isopropanol and taken up in 300 ml of dimethylformamide. Then, 69 g (500 mmol) of potassium carbonate as well as 97 g (500 mmol) of bromoacetic acid-tert-butyl ester are added to it and the 4-benzyl-1,4,7-triazaheptane is alkylated at room temperature overnight. Then, the dimethylformamide is drawn off in an oil pump vacuum, the residue is dispersed between water and dichloromethane, the organic solution is dried on sodium sulfate, evaporated to dryness in a vacuum and the residue is purified by chromatography on silica gel. The title compound is eluted with ethyl acetate/hexane. It is obtained as foam.

Yield: 59.85 g (92.1% of theory)

Elementary analysis: Cld: C 64.69 H 9.15 N 6.47 Fnd: C 64.75 H 9.23 N 6.44 c) 3,9-Bis(tert-butoxycarbonylmethyl)-3,6,9-triazaundecanedicarboxylic acid-di-tert-butyl ester 6.50 g (10 mmol) of the compound produced under 3b) is dissolved in 100 ml of ethanol, mixed with 400 mg of Pearlman's catalyst (Pd 20%, C) and hydrogenated until 224 ml of hydrogen is taken up. It is suctioned off from the catalyst, rewashed with ethanol and evaporated to dryness in a vacuum. The title compound is obtained as white foam.

Yield: 5.58 g (99.5% of theory)

Elementary analysis: Cld: C 60.08 H 9.54 N 7.51 Fnd: C 60.17 H 9.60 N 7.57 d) 3,9-Bis(tert-butoxycarbonylmethyl)-6-(2-isopropyl)-ethoxycarbonylmethyl-3,6,9-triazaundecanedioic acid-di-tert-butyl ester 5.60 g (10 mmol) of the amino compound produced under Example 3c) is dissolved in 30 ml of dimethylformamide. Then, 1.66 g (12 mmol) of potassium carbonate as well as 2.0 g (12 mmol) of 2-bromo-2-isopropylacetic acid ethyl ester are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 4.07 g (59.2% of theory)

Elementary analysis: Cld: C 61.11 H 9.52 N 6.11 Fnd: C 61.03 H 9.60 N 6.17 e) 3,9-Bis(tert-butoxycarbonylmethyl)-6-(2-isopropyl)-carboxymethyl-3,6,9-triazaundecanedioic acid-di-tert-butyl ester 6.88 g (10 mmol) of the compound produced under Example 3d) is dissolved in 50 ml of ethanol. The solution of 400 mg (10 mmol) of sodium hydroxide in 5 ml of distilled water is then added to it and stirred for 3 hours at 50° C. According to the thin-layer chromatogram, saponification is quantitative. It is evaporated to dryness in a vacuum, traces of water are removed by codistillation with ethanol, and the residue is dried at 40° C. in a vacuum. The title compound is obtained as white powder. The remaining white residue is dissolved in 80 ml of wet ethanol (9:1) and mixed with stirring with the solution of 535 mg (10 mmol) of ammonium chloride in 10 ml of distilled water. It is evaporated to dryness in a vacuum, the soluble portions are taken up in butanol and evaporated to dryness again in a vacuum. The residue is extracted with toluene. The organic solution is evaporated to dryness in a vacuum and the title compound is obtained from hexane.

Yield: 5.53 g (83.8% of theory)

Elementary analysis: Cld: C 60.07 H 9.32 N 6.37 Fnd: C 60.18 H 9.41 N 6.44 f) 3,9-Bis(tert-butoxycarbonylmethyl)-6-(2-isopropyl)-N-morpholinocarbonylmethyl-3,6,9-triazaundecanedioic acid-di-tert-butyl ester 5 g (7.58 mmol) of the title compound of Example 3e) and 660 mg (7.58 mmol) of morpholine are dissolved in 30 ml of toluene and 2.06 g (8.34 mmol) of 2-ethoxy-1-ethoxycarbonyl-1,2-dihydroquinoline is added at 0° C. It is stirred for 30 minutes at 0° C., then overnight at room temperature. It is evaporated to dryness in a vacuum and the residue is chromatographed on silica gel (mobile solvent: hexane/ethyl acetate=15:1).

Yield: 5.14 g (93% of theory) of a colorless oil

Elementary analysis: Cld: C 60.96 H 9.40 N 7.69 Fnd: C 60.87 H 9.51 N 7.60 g) 3,9-Bis(tert-carboxymethyl)-6-(2-isopropyl)-N-morpholinocarbonylmethyl-3,6,9-triazaundecanedioic acid 5.00 g (6.86 mmol) of the title compound of Example 3f) is dissolved in 100 ml of trifluoroacetic acid. It is stirred overnight at room temperature. It is evaporated to dryness in a vacuum and the residue is chromatographed on silica gel (mobile solvent: ethanol/25% ammonia water 20:1). The fractions containing the product are evaporated to dryness in a vacuum. The residue is dissolved in 100 ml of water. 20 ml of acid ion exchanger IR 120 ($H^+$ form) is (added and stirred for added and stirred for 10 minutes at room temperature. It is filtered off from the ion exchanger and evaporated to dryness in a vacuum.

Yield: 2.59 g (71% of theory) of a vitreous solid

Water content: 5.3%

Elementary analysis (relative to anhydrous substance): Cld: C 49.99 H 7.19 N 11.11 Fnd: C 49.85 H 7.25 N 11.03

Example 4

3,9-Bis(tert-butoxycarbonylmethyl)-6-(2-phenyl)-carboxymethyl-3,6,9-triazaundecanedioic acid-di-tert-butyl ester a) 1,7-Bis(phthalimido)-4-benzyl-1,4,7-triazaheptane 36.34 g (100 mmol) of 1,7-bis(phthalimido)-1,4,7-triazaheptane [produced according to J. Org. Chem. USSR, 23: 3302 (1987)]is dissolved in 500 ml of dimethylformamide. Then, 16.6 g (120 mmol) of potassium carbonate as well as 20.53 g (120 mmol) of benzyl bromide are added to it and stirred overnight at 25° C. It is poured in ice water, the precipitated product is suctioned off, rewashed with water, taken up in 1,2-dichloroethane, dried on sodium sulfate and evaporated to dryness in a vacuum. The title compound is obtained as solid.

Yield: 42.76 g (94.3% of theory)

Elementary analysis: Cld: C 71.51 H 5.11 N 9.27 Fnd: C 71.40 H 5.18 N 9.38 b) 3,9-Bis(tert-butoxycarbonylmethyl)-6-benzyl-3,6,9-triazaundecanedioic acid-di-tert-butyl ester 22.68 g (50 mmol) of the compound produced under 4a) is added in portions with stirring in 250 ml of hydrazine hydrate. It is heated for 4 more hours to 60° C., allowed to cool off, suctioned off from phthalhydrazide, rewashed with hydrazine hydrate and concentrated by evaporation in a vacuum. The residue is freed from hydrazine residues by codistillation with isopropanol. The 4-benzyl-1,4,7-triazaheptane is taken up in 150 ml of dimethylformamide, 34.5 g (250 mmol) of potassium carbonate is added to it and finally 48.5 g (250 mmol) of bromoacetic acid-tert-butyl ester. The alkylation is allowed to be in progress overnight at room temperature. Then, the dimethylformamide is drawn off in an oil pump vacuum, the residue is dispersed between water and dichloromethane, dried on sodium sulfate, evaporated to dryness in a vacuum and the residue is purified by chromatography on silica gel. The title compound is obtained as foam.

Yield: 51.15 g (78.7% of theory)

Elementary analysis: Cld: C 64.69 H 9.15 N 6.47 Fnd: C 64.60 H 9.20 N 6.53 c) 3,9-Bis(tert-butoxycarbonylmethyl)-3,6,9-triazaundecanedicarboxylic acid-di-tert-butyl ester 13.0 g (20 mmol) of the compound produced under 4b) is dissolved in 200 ml of ethanol, mixed with 0.8 g of Pearlman's catalyst (Pd 20%, C) and hydrogenated until 448 ml of hydrogen is taken up. It is suctioned off from the catalyst, rewashed with ethanol and evaporated to dryness in a vacuum. The title compound is obtained as foam.

Yield: 5.52 g (98.7% of theory)

Elementary analysis: Cld: C 60.08 H 9.54 N 7.51 Fnd: C 60.01 H 9.62 N 7.58 d) 3,9-Bis(tert-butoxycarbonylmethyl)-6-(2-phenyl)-methoxycarbonylmethyl-3,6,9-triazaundecanedioic acid-di-tert-butyl ester 5.60 g (10 mmol) of the amino compound produced under Example 4c) is dissolved in 30 ml of dimethylformamide. Then, 1.66 g (12 mmol) of potassium carbonate as well as 2.22 g (12 mmol) of 2-chlorophenylacetic acid methyl ester are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 4.40 g (62.1% of theory)

Elementary analysis: Cld: C 62.78 H 8.69 N 5.94 Fnd: C 62.89 H 8.76 N 5.88 e) 3,9-Bis(tert-butoxycarbonylmethyl)-6-(2-phenyl)-carboxymethyl-3,6,9-triazaundecanedioic acid-di-tert-butyl ester 7.08 g (10 mmol) of the compound produced under Example 4d) is dissolved in 50 ml of ethanol. The solution of 400 mg (10 mmol) of sodium hydroxide in 5 ml of distilled water is then added to it and stirred for 3 hours at 50° C. According to the thin-layer chromatogram, saponification is quantitative. It is evaporated to dryness in a vacuum, traces of water are removed by codistillation with ethanol, and the residue is dried at 40° C. in a vacuum. The title compound is obtained as white powder. The remaining white residue is dissolved in 80 ml of wet ethanol (9:1) and mixed with stirring with the solution of 535 mg (10 mmol) of ammonium chloride in 10 ml of distilled water. It is evaporated to dryness in a vacuum, the soluble portions are taken up in butanol and evaporated to dryness again in a vacuum. The residue is extracted with toluene. The organic solution is evaporated to dryness in a vacuum and the title compound is obtained as foam.

Yield: 5.99 g (86.3% of theory)

Elementary analysis: Cld: C 62.32 H 8.57 N 6.06 Fnd: C 62.40 H 8.65 N 6.02 f) 3,9-Bis(tert-butoxycarbonylmethyl)-6-(2-phenyl)-(6'-hydroxyhexyl)-aminocarboxymethyl-3,6,9-triazaundecanedioic acid-di-tert-butyl ester 5 g (7.21 mmol) of the title compound of Example 4e) and 845 mg (7.21 mmol) of 6-aminohexan-1-ol are dissolved in 30 ml of toluene and 1.96 g (7.93 mmol) of 2-ethoxy-1-ethoxycarbonyl-1,2-dihydroquinoline is added at 0° C. It is stirred for 30 minutes at 0° C., then overnight at room temperature. It is evaporated to dryness in a vacuum and the residue is chromatographed on silica gel (mobile solvent: hexane/isopropanol=20:1). 4.52 g (79% of theory) of a colorless oil is obtained.

Elementary analysis (relative to anhydrous substance): Cld: C 63.61 H 9.15 N 7.06 Fnd: C 63.75 H 9.27 N 6.95 g) 3,9-Bis(carboxymethyl)-6-(2-phenyl)-(6'-hydroxyhexyl)-aminocarbonylmethyl-3,6,9-triazaundecanedioic acid 4 g (5.04 mmol) of the title compound of Example 4f) is dissolved in 100 ml of trifluoroacetic acid. It is stirred overnight at room temperature. It is evaporated to dryness in a vacuum and the residue is chromatographed on silica gel (mobile solvent: ethanol/25% ammonia water 20:1). The fractions containing the product are evaporated to dryness in a vacuum. The residue is dissolved in 100 ml of water. 16 ml of acid ion exchanger IR 120 ($H^+$ form) is added and stirred for 10 minutes at room temperature. It is filtered off from the ion exchanger and evaporated to dryness in a vacuum.

Yield: 2.22 g (73% of theory) of a vitreous solid

Water content: 5.8%

Elementary analysis (relative to anhydrous substance): Cld: C 54.92 H 7.09 N 9.85 Fnd: C 54.87 H 7.18 N 9.77

Example 5

3,9-Bis(tert-butoxycarbonylmethyl)-6-[2-(4-methoxyphenyl)]-carboxymethyl-3,6,9-triazaundecanedioic acid-di-tert-butyl ester a) 2-Bromo-2-(4-methoxyphenyl)-acetic acid methyl ester 27.01 g (169 mmol) of bromine is added with intensive stirring to a mixture of 18.46 g (100 mmol) of 2-(4-methoxyphenyl)-acetic acid chloride and 1.24 g (40 mmol) of red phosphorus, so that the bromine coloring fades away steadily. After about half the amount of bromine is added, it is heated for 3 more hours at 40° C. 4.49 g (140 mmol) of methanol is then instilled in the cooled solution, it is allowed to stir for one more hour, diluted with 100 ml of dichloromethane, the solution is instilled with intensive stirring in ice water, the organic phase is separated, washed with saturated sodium carbonate solution and dried on sodium sulfate and evaporated to dryness in a vacuum. The residue is purified by distillation in a bulb tube in the oil pump vacuum.

Yield: 19.59 g (75.6% of theory)

Elementary analysis: Cld: C 46.36 H 4.28 Br 30.84 Fnd: C 46.42 H 4.35 Br 30.78 b) 3,9-Bis(tert-butoxycarbonylmethyl)-6-[2-(4-methoxyphenyl)]-methoxy-carbonylmethyl-3,6,9-triazaundecanedioic acid-di-tert-butyl ester 5.60 g (10 mmol) of the amino compound produced under Example 1d) is dissolved in 30 ml of dimethylformamide.

Then, 1.66 g (12 mmol) of potassium carbonate as well as 3.11 g (12 mmol) of 2-bromo-2-(4-methoxyphenylacetic acid methyl ester) are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 5.50 g (74.6% of theory)

Elementary analysis: Cld: C 61.85 H 8.60 N 5.69 Fnd: C 61.78 H 8.66 N 5.75 c) 3,9-Bis(tert-butoxycarbonylmethyl)-6-[2-(4-methoxyphenyl)]-carboxymethyl-3,6,9-triazaundecanedioic acid-di-tert-butyl ester 7.38 g (10 mmol) of the compound produced under Example 5b) is dissolved in 50 ml of ethanol. The solution of 400 mg (10 mmol) of sodium hydroxide in 5 ml of distilled water is then added to it and stirred for 3 hours at 50° C. According to the thin-layer chromatogram, saponification is quantitative. It is evaporated to dryness in a vacuum, traces of water are removed by codistillation with ethanol and the residue is dried at 40° C. in a vacuum. The title compound is obtained as white powder. The remaining white residue is dissolved in 80 ml of wet ethanol (9:1) and mixed with stirring with the solution of 535 mg (10 mmol) of ammonium chloride in 10 ml of distilled water. It is evaporated to dryness in a vacuum, the soluble portions are taken up in butanol and evaporated to dryness again in a vacuum. The residue is extracted with toluene. The organic solution is evaporated to dryness in a vacuum and the title compound is obtained as foam.

Yield: 6.39 g (88.3% Of theory)

Elementary analysis: Cld: C 61.39 H 8.49 N 5.80 Fnd: C 61.31 H 8.56 N 5.74 d) 3,9-Bis(tert-butoxycarbonylmethyl)-6-[2-(4-methoxyphenyl)]-aminocarbonylmethyl-3,6,9-triazaundecanedioic acid-di-tert-butyl ester 5 g (6.91 mmol) of the title compound of Example 5c) is dissolved in 30 ml of anhydrous benzene and 1.75 g (13.82 mmol) of oxalic acid dichloride is added at 0° C. It is stirred for 3 hours at 0° C. and then evaporated to dryness in a vacuum. The residue is dissolved in 30 ml of benzene and again evaporated to dryness. At 0° C., ammonia gas is introduced into the solution with vigorous stirring (30 minutes). The solution is washed twice with 50 ml of 5% aqueous soda solution in each case, the organic phase is dried on magnesium sulfate and evaporated to dryness in a vacuum. The residue is chromatographed on silica gel (mobile solvent: methylene chloride/hexane/isopropanol= 10:10:1).

Yield: 3.95 g (79% of theory) of a colorless solid

Elementary analysis: Cld: C 61.47 H 8.64 N 7.75 Fnd: C 61.58 H 8.75 N 7.61 e) 3,9-Bis(carboxymethyl)-6-[2-(4-methoxyphenyl)]-aminocarbonylmethyl-3,6,9-triazaundecanedioic acid 3.5 g (4.84 mmol) of the title compound of Example 5d) is dissolved in 100 ml of trifluoroacetic acid. It is stirred overnight at room temperature. It is evaporated to dryness in a vacuum and the residue is chromatographed on silica gel (mobile solvent: ethanol/25% ammonia water 20:1). The fractions containing the product are evaporated to dryness in a vacuum. The residue is dissolved in 100 ml of water. 15 ml of acid ion exchanger IR 120 ($H^+$ form) is added and stirred for 10 minutes at room temperature. It is filtered off from the ion exchanger and evaporated to dryness in a vacuum.

Yield: 1.60 g (63% of theory) of a vitreous solid

Water content: 5.0%

Elementary analysis (relative to anhydrous substance): Cld: C 50.60 H 6.07 N 11.24 Fnd: C 50.70 H 6.15 N 11.13

Example 6

3,9-Bis(tert-butoxycarbonylmethyl)-6-[2-(4-ethoxybenzyl)-carboxymethyl-3,6,9-triazaundecanedioic acid-di-tert-butyl ester 2-Bromo-3-(4-ethoxyphenyl)-propionic acid ethyl ester a) 3-(4-Ethoxyphenyl)-propionic acid 16.62 g (100 mmol) of 3-(4-hydroxyphenyl)-propionic acid is dissolved with stirring and covering with argon in 45 ml (225.0 mmol) of 5 N sodium hydroxide solution, and 15.73 g (100 mmol), (98%) of diethyl sulfate is instilled quickly so that the temperature does not exceed 40° C. (water cooling). After completion of the addition, it is heated for 30 more minutes to 100° C. After the cooling, it is extracted with diethyl ether, then acidified with sulfuric acid to pH 4 and the precipitated compound is taken up in ether. After drying on sodium sulfate, it is evaporated to dryness in a vacuum. The title compound is obtained as solid.

Yield: 15.21 g (78.3% of theory)

Elementary analysis: Cld: C 68.02 H 7.26 Fnd: C 68.13 H 7.34 b) 2-Bromo-3-(4-ethoxyphenyl)-propionic acid ethyl ester

A drop of dimethylformamide is added to 9.71 g (50 mmol) of the acid, produced under 6a), in 50 ml of 1,2-dichloroethane. Then, it is heated to 80° C. and 5.0 ml (68.6 mmol) of thionyl chloride is instilled in it. Vigorous gas generation takes place. After completion of the addition, it is refluxed for one more hour, then evaporated to dryness in a vacuum and 0.62 g (20 mmol) of red phosphorus is added to the acid chloride. Then, 13.6 g (85 mmol) of bromine is quickly instilled with stirring so that the bromine coloring simply fades away. When about half the amount of bromine is added, it is heated to 40° C. and the temperature is maintained for three hours. It is cooled to room temperature and then 3.22 g (70 mmol) of ethanol in 20 ml of dichloromethane is instilled in it. After one hour, it is diluted with 200 ml of dichloromethane, poured on ice water, the organic solution is separated, washed with saturated sodium bicarbonate solution and evaporated to dryness in a vacuum. The title compound is purified by chromatography on silica gel. A mixture of ethyl acetate and hexane is used as eluant. The title compound is obtained as syrup.

Yield: 11.57 g (76.8% of theory)

Elementary analysis: Cld: C 51.84 H 5.69 Br 26.53 Fnd: C 51.77 H 5.74 Br 26.59 c) 3,9-Bis(tert-butoxycarbonylmethyl)-6-[2-(4-ethoxybenzyl)-ethoxycarbonylmethyl-3,6,9-triazaundecanedioic acid-di-tert-butyl ester 5.60 g (10 mmol) of the amino compound produced under Example 1d) is dissolved in 30 ml of dimethylformamide. Then, 1.66 g (12 mmol) of potassium carbonate as well as 3.61 g (12 mmol) of 2-bromo-2-(4-ethoxybenzyl)-acetic acid ethyl ester are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 4.95 g (63.4% of theory)

Elementary analysis: Cld: C 63.13 H 8.92 N 5.39 Fnd: C 63.07 H 8.89 N 5.44 d) 3,9-Bis(tert-butoxycarbonylmethyl)-6-[2-(4-ethoxybenzyl)-carboxymethyl-3,6,9-triazaundecanedioic acid-di-tert-butyl ester 7.80 g (10 mmol) of the compound produced under Example 6c) is dissolved in 50 ml of ethanol. The solution of 400 mg (10 mmol) of sodium hydroxide in 5 ml of distilled water is then added to it and stirred for 3 hours at 50° C. According to the thin-layer chromatogram, saponification is quantitative. It is evaporated to dryness in a vacuum, traces of water are removed by codistillation with ethanol and the residue is dried at 40° C. in a vacuum. The title compound is obtained as white powder. The remaining white residue is dissolved in 80 ml of wet ethanol (9:1) and mixed with stirring with the solution of 535 mg (10 mmol) of ammonium chloride in 10 ml of distilled water. It is evaporated to dryness in a vacuum, the soluble portions are taken up in butanol and evaporated to dryness again in a vacuum. The residue is extracted with toluene. The organic solution is evaporated to dryness in a vacuum and the title compound is obtained as foam.

Yield: 6.47 g (86.1% of theory)

Elementary analysis: Cld: C 62.29 H 8.71 N 5.59 Fnd: C 62.36 H 8.77 N 5.57 e) 3,9-Bis(tert-butoxycarbonylmethyl)-6-[2-(4-ethoxybenzyl)]-aminocarboxymethyl-3,6,9-triazaundecanedioic acid-di-tert-butyl ester 5 g (6.65 mmol) of the title compound of Example 6d) is dissolved in 30 ml of anhydrous benzene and 1.69 g (13.30 mmol) of oxalic acid dichloride is added at 0° C. It is stirred for 3 hours at 0° C. and then evaporated to dryness in a vacuum. The residue is dissolved in 30 ml of benzene and again evaporated to dryness. At 0° C., ammonia gas is introduced in the solution with vigorous stirring (30 minutes). The solution is washed twice with 50 ml of 5% aqueous soda solution in each case, the organic phase is dried on magnesium sulfate and evaporated to dryness in a vacuum. The residue is chromatographed on silica gel (mobile solvent: methylene chloride/hexane/isopropanol= 10:1)

Yield: 4.05 g (81% of theory) of a colorless solid

Elementary analysis: Cld: C 62.38 H 8.86 N 7.46 Fnd: C 62.45 H 8.78 N 7.35 f) 3,9-Bis(carboxymethyl)-6-[2-(4-ethoxybenzyl)-aminocarboxymethyl-3,6,9-triazaundecanedioic acid 4.00 g (5.32 mmol) of the title compound of Example 6e) is dissolved in 100 ml of trifluoroacetic acid. It is stirred overnight at room temperature. It is evaporated to dryness in a vacuum and the residue is chromatographed on silica gel (mobile solvent: ethanol/25% ammonia water 20:1). The fractions containing the product are evaporated to dryness in a vacuum. The residue is dissolved in 100 ml of water. 15 ml of acid ion exchanger IR 120 ($H^+$ form) is added and stirred for 10 minutes at room temperature. It is filtered off from the ion exchanger and evaporated to dryness in a vacuum.

Yield: 1.90 g (64% of theory) of a vitreous solid

Water content: 5.7%

Elementary analysis (relative to anhydrous substance): Cld: C 52.47 H 6.51 N 10.64 Fnd: C 52.38 H 6.60 N 10.58

Example 7

3,9-Bis(tert-butoxycarbonylmethyl)-6-[2-(pyrid-2-yl)]-ethoxycarbonylmethyl-3,6,9-triazaundecanedioic acid-di-tert-butyl ester a) 2-Bromo-2-(pyrid-2-yl)-acetic acid ethyl ester 16.52 g (100 mmol) of 2-pyridylacetic acid ethyl ester is dissolved in 50 ml of carbon tetrachloride. It is cooled to 0° C. and 15.98 g (100 mmol) of bromine, dissolved in 15 ml of carbon tetrachloride, is then instilled in it within 30 minutes. Then, it is allowed to react for one more hour at 25° C. The bromine coloring fades away. It is concentrated by evaporation in a vacuum and the hydrobromide of the title compound is obtained. The free compound is obtained by extraction of ether from the aqueous solution after the addition of sodium bicarbonate.

Yield: 22.80 g (93.4% of theory)

Elementary analysis: Cld: C 44.29 H 4.13 Br 32.74 N 5.74 Fnd: C 44.22 H 4.18 Br 32.81 N 5.68 b) 3,9-Bis(tert-butoxycarbonylmethyl)-6-[2-(pyrid-2-yl)]-ethoxycarbonylmethyl-3,6,9-triazaundecanedioic acid-di-tert-butyl ester 5.60 g (10 mmol) of the amino compound produced under Example 1d) is dissolved in 30 ml of dimethylformamide. Then, 1.66 g (12 mmol) of potassium carbonate as well as 2.93 g (12 mmol) of 2-bromo-2-(pyrid-2-yl)-acetic acid ethyl ester are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 5.11 g (69.2% of theory)

Elementary analysis: Cld: C 60.14 H 8.46 N 7.58 Fnd: C 60.21 H 8.55 N 7.66 c) 3,9-Bis(tert-butoxycarbonylmethyl)-6-[2-(pyrid-2-yl)]-carboxymethyl-3,6,9-triazaundecanedioic acid-butyl ester 7.39 g (10 mmol) of the compound produced under Example 7b) is dissolved in 50 ml of ethanol. The solution of 400 mg (10 mmol) of sodium hydroxide in 5 ml of distilled water is then added to it and stirred for 3 hours at 50° C. According to the thin-layer chromatogram, saponification is quantitative. It is evaporated to dryness in a vacuum, traces of water are removed by codistillation with ethanol and the residue is dried at 40° C. in a vacuum. The title compound is obtained as white powder. The remaining white residue is dissolved in 80 ml of wet ethanol (9:1) and mixed with stirring with the solution of 535 mg (10 mmol) of ammonium chloride in 10 ml of distilled water. It is evaporated to dryness in a vacuum, the soluble portions are taken up in butanol and evaporated to dryness again in a vacuum. The residue is extracted with toluene. The organic solution is evaporated to dryness in a vacuum and the title compound is obtained as foam.

Yield: 5.96 g (87.6% of theory)

Elementary analysis: Cld: C 61.74 H 6.59 N 6.17 Fnd: C 61.66 H 6.65 N 6.24 d) 3,9-Bis(tertobutoxycarbonylmethyl)-6-[2-(pyridyl-2-yl)]-(4-carboxybutyl)aminocarbonylmethyl-3,6,9-triazaundecanedioic acid-di-tert-butyl ester 5 g (7.34 mmol) of the title compound of Example 7c) and 0.74 g (7.34 mmol) of triethylamine are dissolved in 50 ml of methylene chloride. At −10° C., a solution of 1.11 g (8.1 mmol) of isobutyl chloroformate in 10 ml of methyl chloride is instilled within 5 minutes and stirred for 20 minutes at −10° C. The solution is cooled off to −15° C. and a solution of 0.86 g (7.34 mmol) of 5-aminopentanoic acid and 2.23 g (22.0 mmol) of triethylamine in 10 ml of methylene chloride is instilled within 10 minutes and stirred for 30 minutes at −15° C., then overnight at room temperature. It is extracted twice with 100 ml each of 10% aqueous ammonium chloride solution, the organic phase is dried on magnesium sulfate and evaporated to dryness in a vacuum. The residue is chromatographed on silica gel (mobile solvent: methylene chloride/ethanol=20:1).

Yield: 4.60 g (79% of theory) of a colorless solid

Elementary analysis: Cld: C 60.51 H 8.50 N 8.82 Fnd: C 60.63 H 8.60 N 8.71 e) 3,9-Bis(carboxymethyl)-6-[2-(pyridyl-2-yl)]-(4-carboxybutyl)aminocarbonylmethyl-3,6,9-triazaundecanedioic acid 4.50 g (5.67 mmol) of the title compound of Example 7d) is dissolved in 100 ml of trifluoroacetic acid. It is stirred overnight at room temperature. It is evaporated to dryness in a vacuum and the residue is chromatographed on silica gel (mobile solvent: ethanol/25% ammonia water 20:1). The fractions containing the product are evaporated to dryness in a vacuum. The residue is dissolved in 100 ml of water. 20 ml of acid ion exchanger IR 120 (H$^+$ form) is added and stirred for 10 minutes at room temperature. It is filtered off from the ion exchanger and evaporated to dryness in a vacuum.

Yield: 2.07 9 (59% of theory) of a vitreous solid
Water content: 8.1%
Elementary analysis (relative to anhydrous substance):
Cld: C 50.61 H 6.19 N 12.30 Fnd: C 50.50 H 6.27 N 12.36

Example 8

3,9-Bis(tert-butoxycarbonylmethyl)-6-[2-(2,5-dioxahexyl)]-carboxymethyl-3,6,9-triazaundecanedioic acid-di-tert-butyl ester a) 4,7-Dioxaoctanoic acid benzyl ester 1.15 g (50.0 mmol) of sodium is dissolved in 100 ml of dried ethylene glycol monomethyl ether. Then, 5.01 g (50 mmol) of freshly distilled ethyl acrylate, dissolved in 15 ml of dry diethyl ether at 0° C., is instilled in it with stirring and exclusion of moisture. It is allowed to stir for 1 more hour at the low temperature, then 5 ml of water is added to it and heated for 2 hours to 60° C. to saponify the ester. It is concentrated by evaporation in a vacuum to 30 ml, diluted with 100 ml of water, the solution is extracted with ether and then the aqueous phase is adjusted with sulfuric acid to pH 4. The precipitated compound is taken up in diethyl ether, the solution is dried on sodium sulfate and evaporated to dryness in a vacuum. The title compound is obtained as syrup.

Yield: 6.11 g (82.5% of theory)
Elementary analysis: Cld: C 48.64 H 8.16 Fnd: C 48.71 H 8.23 b) 2-Bromo-4,7-dioxaoctanoic acid benzyl ester

One drop of dimethylformamide is added to 7.41 g (50 mmol) of the acid, produced under Example 8a), in 50 ml of 1,2-dichloroethane. Then, it is heated to 80° C. and 5.0 ml (68.6 mmol) of thionyl chloride is instilled in it. Vigorous gas generation takes place. After completion of the addition, it is refluxed for one more hour and then evaporated to dryness in a vacuum. 0.62 g (20 mmol) of red phosphorus is added to the acid chloride and then 13.6 g (85 mmol) of bromine is quickly instilled with stirring so that the bromine coloring simply fades away. When about half the amount of bromine is added, it is heated to 40° C. and this temperature is maintained for three more hours. It is cooled to room temperature and the mixture of 7.57 g (70 mmol) of benzyl alcohol and 7.08 g (70 mmol) of dry triethylamine in 20 ml of dichloromethane is instilled in it. After 1 hour, it is diluted with 200 ml of dichloromethane, poured on ice water and the organic solution is separated. It is washed with saturated sodium bicarbonate solution, dried on sodium sulfate and evaporated to dryness in a vacuum. The title compound is purified by chromatography on silica gel. A mixture of ethyl acetate and hexane is used as eluant. The title compound is obtained as syrup.

Yield: 12.43 g (78.4% of theory)
Elementary analysis: Cld: C 49.23 H 5.40 Br 25.19 Fnd: C 49.30 H 5.46 Br 25.10 c) 3,9-Bis(tert-butoxycarbonylmethyl)-6-[2-(2,5-dioxahexyl)]-benzyloxy-carbonylmethyl-3,6,9-triazaundecanedioic acid-diotert-butyl ester 5.60 g (10 mmol) of the amino compound produced under Example 1d) is dissolved in 30 ml of dimethylformamide. Then, 1.66 g (12 mmol) of potassium carbonate as well as 3.81 g (12 mmol) of 2-bromo-4,7-dioxaoctanoic acid benzyl ester are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 5.20 g (65.2% of theory)
Elementary analysis: Cld: C 61.79 H 8.85 N 5.27 Fnd: C 61.87 H 8.92 N 5.22 d) 3,9-Bis(tert-butoxycarbonylmethyl)-6-[2-(2,5-dioxahexyl)]-carboxymethyl-3,6,9-triazaundecanedioic acid-di-tert-butyl ester 7.97 g (10 mmol) of the benzyl ester produced under 8c) is dissolved in 100 ml of ethanol and mixed with 0.4 g of Pearlman's catalyst (Pd 20%, C). It is hydrogenated until 224 ml of hydrogen is taken up, then suctioned off from the catalyst, washed well with ethanol and the solution is evaporated to dryness in a vacuum. The product is obtained as foam.

Yield: 6.87 g (97.3% of theory)
Elementary analysis: Cld: C 57.85 H 9.00 N 5.95 Fnd: C 57.91 H 9.11 N 6.01 e) 3,9-Bis(tert-butoxycarbonylmethyl)-6-[2-(2,5-dioxahexyl)]-(2-hydroxyethyl)-aminocarbonylmethyl-3,6,9-triazaundecanedioic acid-di-tert-butyl ester 5 g (7.08 mmol) of the title compound of Example 8d) and 476 mg (7.08 mmol) of ethanolamine are dissolved in 30 ml of toluene and 1.93 g (7.79 mmol) of 2-ethoxy-1-ethoxycarbonyl-1,2-dihydroquinoline is added at 0° C. It is stirred for 30 minutes at 0° C., then overnight at room temperature. It is evaporated to dryness in a vacuum and the residue is chromatographed on silica gel (mobile solvent: hexane/ethyl acetate=15:1).

Yield: 4.93 g (93% of theory) of a colorless oil
Elementary analysis: Cld: C 57.73 H 9.15 N 7.48 Fnd: C 57.61 H 9.23 N 7.35 f) 3,9-Bis(carboxymethyl)-6-[2-(2,5-dioxahexyl)]-(2-hydroxyethyl)-aminocarbonylmethyl-3,6,9-triazaundecanedioic acid 4.5 g (6.01 mmol) of the title compound of Example 8f) is dissolved in 100 ml of trifluoroacetic acid. It is stirred overnight at room temperature. It is evaporated to dryness in a vacuum and the residue is chromatographed on silica gel (mobile solvent: ethanol/25% ammonia water 20:1). The fractions containing the product are evaporated to dryness in a vacuum. The residue is dissolved in 100 ml of water. 20 ml of acid ion exchanger IR 120 (H$^+$ form) is added and stirred for 10 minutes at room temperature. It is filtered off from the ion exchanger and evaporated to dryness in a vacuum.

Yield: 2.50 g (72% of theory) of a vitreous solid
Water content: 9.1%
Elementary analysis: Cld: C 45.80 H 6.92 N 10.68 Fnd: C 45.93 H 6.84 N 10.75

Example 9

3,9-Bis(tert-butoxycarbonylmethyl)-6-(2-hydroxymethyl)-carboxymethyl-3,6,9-triazaundecanedioic acid-di-tert-butyl ester a) 3-Benzyloxy-2-bromopropionic acid methyl ester 40.3 g (339 mmol) of potassium bromide is dissolved in 200 ml of 2.5 N sulfuric acid. 19.52 g (100 mmol) of 3-benzyloxy-serine is added to it, cooled to 0° C. and 10.6 g (154 mmol) of sodium nitrite is added in the course of one hour with vigorous stirring. It is allowed to stir for one more hour at 0° C. and for another at 25° C. Then, it is extracted with ether, the solution is washed with water, dried on sodium sulfate and the carboxylic acid is esterified by adding an ethereal diazomethane solution in portions until the reaction is discernibly completed (coloring, TLC control). The solution is concentrated by evaporation in a vacuum. The title compound is purified by chromatography on silica gel with a mixture of ether and hexane as eluant. It is obtained as oil.

Yield: 22.97 g (84.1% of theory)

Elementary analysis: Cld: C 48.37 H 4.80 Br 29.26 Fnd: C 48.30 H 4.86 Br 29.33 b) 3,9-Bis(tert-butoxycarbonylmethyl)-6-[2-(benzyloxymethyl)]-ethoxycarbonylmethyl-3,6,9-triazaundecanedioic acid-di-tert-butyl ester 5.60 g (10 mmol) of the amino compound produced under Example 1d) is dissolved in 30 ml of dimethylformamide. Then, 1.66 g (12 mmol) of potassium carbonate as well as 3.28 g (12 mmol) of 2-bromo-3-benzyloxypropionic acid benzyl ester are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 5.09 g (67.1% of theory)

Elementary analysis: Cld: C 63.39 H 7.85 N 5.54 Fnd: C 63.51 H 7.90 N 5.59 c) 3,9-Bis(tert-butoxycarbonylmethyl)-6-(2-hydroxymethyl)-carboxymethyl)-3,6,9-triazaundecanedioic acid-di-tert-butyl ester 7.52 g (10 mmol) of the benzyl ether produced under 9b) is dissolved in 100 ml of ethanol and mixed with 0.4 g of Pearlman's catalyst (Pd 20%, C). It is hydrogenated until 224 ml of hydrogen is taken up, then suctioned off from the catalyst, rewashed well with ethanol and evaporated to dryness in a vacuum. The product is obtained as foam.

Yield: 5.71 g (88.1% of theory)

Elementary analysis: Cld: C 57.48 H 8.87 N 6.49 Fnd: C 57.60 H 8.98 N 6.59 d) 3,9-Bis(tert-butoxycarbonylmethyl)-6-(2-hydroxymethyl)-(2,2-dimethyl-6-hydroxy-1,3-dioxepan-5-yl)-aminocarbonylmethyl-3,6,9-triazaundecanedioic acid-di-tert-butyl ester 5 g (7.72 mmol) of the title compound of Example 9c) and 781 mg (7.72 mmol) of triethylamine are dissolved in 50 ml of methylene chloride. At −10° C., a solution of 1.16 g (8.5 mmol) of isobutyl chloroformate in 10 ml of methyl chloride is instilled within 5 minutes and stirred for 20 minutes at −10° C. The solution is cooled off to −15° C. and a solution of 1.24 g (7.72 mmol) of 5-amino-2,2-dimethyl-1,3-dioxepan-6-ol and 2.12 g (21 mmol) of triethylamine in 10 ml of methylene chloride is instilled within 10 minutes and stirred for 30 minutes at −15° C., then overnight at room temperature. It is extracted twice with 100 ml each of 10% aqueous ammonium chloride solution, the organic phase is dried on magnesium sulfate and evaporated to dryness in a vacuum. The residue is chromatographed on silica gel (mobile solvent: methylene chloride/ethanol=20:1).

Yield: 4.50 g (79% of theory) of a colorless solid

Elementary analysis: Cld: C 57.70 H 8.92 N 7.08 Fnd: C 57.60 H 9.05 N 7.15 e) 3,9-Bis(carbonylmethyl)-6-(2-hydroxymethyl)-[1-(hydroxymethyl)-2,3-dihydroxypropyl]-aminocarbonylmethyl-3,6,9-triazaundecanedioic acid 4 g (5.06 mmol) of the title compound of Example 9d) is dissolved in 100 ml of trifluoroacetic acid. It is stirred overnight at room temperature. It is evaporated to dryness in a vacuum and the residue is chromatographed on silica gel (mobile solvent: ethanol/25% ammonia water 20:1). The fractions containing the product are evaporated to dryness in a vacuum. The residue is dissolved in 100 ml of water. 20 ml of acid ion exchanger IR 120 ($H^+$ form) is added and stirred for 10 minutes at room temperature. It is filtered off from the ion exchanger and evaporated to dryness in a vacuum.

Yield: 1.76 g (61% of theory) of a vitreous solid

Water content: 7.5%

Elementary analysis (relative to anhydrous substance): Cld: C 43.34 H 6.51 N 10.64 Fnd: C 43.25 H 6.65 N 10.51

Example 10

3,9-Bis(tert-butoxycarbonylmethyl)-6-[2-(4-benzyloxycarbonylamino)-butyl]-carboxymethyl-3,6,9-triazaundecanedioic acid-di-tert-butyl ester a) 3,9-Bis(tert-butoxycarbonylmethyl)-6-[2-(4-bromo)-butyl]-ethoxycarbonylmethyl-3,6,9-triazaundecanedioic acid-di-tert-butyl ester 5.60 g (10 mmol) of the amino compound produced under Example 1d) is dissolved in 30 ml of dimethylformamide. Then, 1.66 g (12 mmol) of potassium carbonate as well as 3.62 g (12 mmol) of 2,6-dibromohexanoic acid ethyl ester are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 4.90 g (62.7% of theory)

Elementary analysis: Cld: C 55.38 H 8.52 Br 10.23 N 5.38 Fnd: C 55.48 H 8.59 Br 10.34 N 5.31 b) 3,9-Bis(tert-butoxycarbonylmethyl)-6-[2-(4-benzyloxycarbonylamino)-butyl]-carboxymethyl-3,6,9-triazaundecanedioic acid-di-tert-butyl ester 7.81 g (10 mmol) of the compound produced under Example 10a) is dissolved in 50 ml of nitromethane and mixed with 1.56 (10.4 mmol) of silver cyanate. It is stirred with exclusion of moisture for 70 hours at room temperature. Then, it is mixed with 1.62 g (15 mmol) of benzyl alcohol and allowed to stir for another 3 hours at room temperature. Then, it is diluted with 200 ml of diethyl ether, filtered off from silver salt, the solution is concentrated by evaporation in a vacuum and the residue is purified by column chromatography on silica gel. A mixture of ethyl acetate and hexane is used as eluant. The title compound is obtained as amorphous foam.

Yield: 5.84 g (68.6% of theory)

Elementary analysis: Cld: C 62.10 H 8.76 N 6.58 Fnd: C 62.23 H 8.83 N 6.67 c) 3,9-Bis(tert-butoxycarbonylmethyl)-6-[2-(4-benzyloxycarbonylamino)-butyl]-aminocarbonylmethyl-3,6,9-triazaundecanedioic acid-di-tert-butyl ester 5 g (6.65 mmol) of the title compound of Example 10b) is dissolved in 30 ml of anhydrous benzene and 1.54 g (12.15 mmol) of oxalic acid dichloride is added at 0° C. It is stirred for 3 hours at 0° C. and then evaporated to dryness in a vacuum. The residue is dissolved in 30 ml of benzene and again evaporated to dryness. At 0° C., ammonia gas is introduced into the solution with vigorous stirring (30 minutes). The solution is washed twice with 50 ml of 5% aqueous soda solution in each case, the organic phase is dried on magnesium sulfate and evaporated to dryness in a vacuum. The residue is chromatographed on silica gel (mobile solvent: methylene chloride/hexane/isopropanol= 10:10:1)

Yield: 4.2 g (84% of theory) of a colorless solid

Elementary analysis: Cld: C 61.37 H 8.71 N 8.52 Fnd: C 61.25 H 8.80 N 8.43 d) 3,9-Bis(tert-butoxycarbonylmethyl)-6-[2-(4-amino)-butyl]-aminocarbonylmethyl-3,6,9-triazaundecanedioic acid-di-tert-butyl ester 4.0 g (4.87 mmol) of the title compound of Example 10c) is dissolved in 100 ml of isopropanol, and 2 g of palladium catalyst (10% Pd on carbon) is added. It is hydrogenated overnight at room temperature. It is filtered off from the catalyst and the filtrate is evaporated to dryness in a vacuum. The residue is chromatographed on silica gel (mobile solvent: methylene chloride/ethanol=25:1).

Yield: 3.05 g (91% of theory) of a colorless oil

Elementary analysis: Cld: C 59.36 H 9.52 N 10.18 Fnd: C 59.27 H 9.61 N 10.27 e) 3,9-Bis(carboxymethyl)-6-[2-(4-amino)-butyl]-aminocarbonylmethyl-3,6,9-triazaundecanedioic acid 3.0 g (4.36 mmol) of the title compound of Example 10d) is dissolved in 100 ml of trifluoroacetic acid. It is stirred overnight at room temperature. It is evaporated to dryness in a vacuum and the residue is chromatographed on silica gel (mobile solvent: ethanol/25% ammonia water 20:1). The fractions containing the product are evaporated to dryness in a vacuum. The residue is dissolved in 100 ml of water. 20 ml of acid ion exchanger IR 120 ($H^+$ form) is added and stirred for 10 minutes at room temperature. It is filtered off from the ion exchanger and evaporated to dryness in a vacuum.

Yield: 1.23 g (57% of theory) of a vitreous solid

Water content: 6.7%

Elementary analysis: Cld: C 46.64 H 7.18 N 15.11 Fnd: C 46.60 H 7.09 N 15.00

Example 11

3,9-Bis(tert-butoxycarbonylmethyl)-6-carboxymethyl-3,6,9-triazaundecanedioic acid-di-tert-butyl ester a) 3,9-Bis(tert-butoxycarbonylmethyl)-6-benzyloxycarbonylmethyl-3,6,9-triazaundecanedioic acid-di-tert-butyl ester 5.60 g (10 mmol) of the amino compound produced under Example 1d) is dissolved in 30 ml of dimethylformamide. Then, 1.66 g (12 mmol) of potassium carbonate as well as 2.58 g (12 mmol) of 2-bromoacetic acid benzyl ester are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 6.32 g (89.3% of theory)

Elementary analysis: Cld: C 64.65 H 9.00 N 5.95 Fnd: C 64.62 H 9.07 N 5.90 b) 3,9-Bis(tert-butoxycarbonylmethyl)-6-carboxymethyl-3,6,9-triazaundecanedioic acid-di-tert-butyl ester 7.08 g (10 mmol) of the benzyl ester produced under 11a) is dissolved in 100 ml of ethanol and mixed with 0.4 g of Pearlman's catalyst (Pd 20%, C). It is hydrogenated until 224 ml of hydrogen is taken up, suctioned off from the catalyst, rewashed well with ethanol and the solution is evaporated to dryness in a vacuum. The product is obtained as foam, which crystallized from ether/hexane.

Yield: 6.87 g (97.3% of theory)

Melting point: 73°–75° C.

Elementary analysis: Cld: C 57.85 H 9.00 N 5.95 Fnd: C 57.91 H 9.11 N 6.01 c) 3,9-Bis(tert-butoxycarbonylmethyl)-6-(2-aminoethyl)-aminocarbonylmethyl-3,6,9-triazaundecanedioic acid-di-tert-butyl ester 5.00 g (8.09 mmol) of the title compound of Example 11b) is dissolved in 25 ml of dimethylformamide, and 1.02 g (8.90 mol) of N-hydroxysuccinimide is added. It is cooled off to 0° C. and 1.84 g (8.90 mmol) of dicyclohexylcarbodiimide is added. It is stirred for 1 hour at 0° C. and then for 4 hours at room temperature. It is cooled off to 0° C. and a solution of 2.67 g of 1.2 diaminoethane (44.5 mmol) in 50 ml of dimethylformamide is instilled within 10 minutes. It is stirred for one hour at 0° C., then overnight at room temperature. It is evaporated to dryness in a vacuum, and the residue is taken up in 100 ml of ethyl acetate. It is filtered off from precipitated urea and the filtrate is washed twice with 100 ml each of 5% aqueous soda solution. The organic phase is dried on magnesium sulfate and evaporated to dryness in a vacuum. The residue is chromatographed on silica gel (mobile solvent: n-hexane/isopropanol 15:1). 2.83 g (53% of theory) of a colorless oil is obtained.

Elementary analysis: Cld: C 58.25 H 9.32 N 10.61 Fnd: C 58.17 H 9.25 N 10.55 d) 3,9-Bis(carboxymethyl)-6-(2-aminoethyl)-aminocarbonylmethyl-3,6,9-triazaundecanedioic acid 2.60 g (3.94 mmol) of the title compound of Example 11c) is dissolved in 100 ml of trifluoroacetic acid. It is stirred overnight at room temperature. It is evaporated to dryness in a vacuum, and the residue is chromatographed on silica gel (mobile solvent: ethanol/25% ammonia water 20:1). The fractions containing the product are evaporated to dryness in a vacuum. The residue is dissolved in 100 ml of water. 15 ml of acid ion exchanger IR 120 ($H^+$ form) is added and stirred for 10 minutes at room temperature. It is filtered off from the ion exchanger and evaporated to dryness in a vacuum.

Yield: 1.29 g (57% of theory) of a vitreous solid

Water content: 7.9%

Elementary analysis (relative to anhydrous substance): Cld: C 44.13 H 6.71 N 16.08 Fnd: C 40.25 H 6.63 N 16.18

Example 12 a) 3,9-Bis(tert-butoxycarbonylmethyl)-6-(3-oxa-5-aminopentyl)-aminocarbonylmethyl-3,6,9-triazaundecanedioic acid-di-tert-butyl ester 5.00 g (8.09 mmol) of the title compound of Example 11b) is dissolved in 25 ml of dimethylformamide, and 1.02 g (8.90 mol) of N-hydroxysuccinimide is added. It is cooled off to 0° C. and 1.84 g (8.90 mmol) of dicyclohexylcarbodiimide is added. It is stirred for 1 hour at 0° C. and then for 4 hours at room temperature. It is cooled off to 0° C. and a solution of 2.67 g of 1.5 diamino-3-oxa-pentane (44.5 mmol) in 50 ml of dimethylformamide is instilled within 10 minutes. It is stirred for one hour at 0° C., then overnight at room temperature. It is evaporated to dryness in a vacuum, and the residue is taken up in 100 ml of ethyl acetate. It is filtered off from precipitated urea and the filtrate is washed twice with 100 ml each of 5% aqueous soda solution. The organic phase is dried on magnesium sulfate and evaporated to dryness in a vacuum. The residue is chromatographed on silica gel (mobile solvent: n-hexane/ethyl acetate 20:1). 2.79 g (49% of theory) of a colorless oil is obtained.

Elementary analysis: Cld: C 58.01 H 9.31 N 9.95 Fnd: C 57.90 H 9.41 N 9.87 b) 3,9-Bis(carboxymethyl)-6-(3-oxa-5-aminopentyl)-aminocarbonylmethyl-3,6,9-triazaundecanedioic acid 2.60 g (3.69 mmol) of the title compound of Example 1g) is dissolved in 100 ml of trifluoroacetic acid. It is stirred overnight at room temperature. It is evaporated to dryness in a vacuum, and the residue is chromatographed on silica gel (mobile solvent: ethanol/25% ammonia water 20:1). The fractions containing the product are evaporated to dryness in a vacuum. The residue is dissolved in 100 ml of water. 20 ml of acid ion exchanger IR 120 ($H^+$ form) is added and stirred for 10 minutes at room temperature. It is filtered off from the ion exchanger and evaporated to dryness in a vacuum.

Yield: 1.11 g (57% of theory) of a vitreous solid
Water content: 8.9%
Elementary analysis: Cld: C 45.09 H 6.94 N 14.61 Fnd: C 45.17 H 6.86 N 14.55

Example 13 a) 3,9-Bis(tert-butoxycarbonylmethyl)-6-bis(octadecyl)-aminocarbonylmethyl-3,6,9-triazaundecanedioic acid-di-tert-butyl ester 5 g (8.09 mmol) of the title compound of Example 11b) and 4.22 g (8.09 mmol) of bis-octadecylamine are dissolved in 30 ml of toluene, and 2.20 g (8.9 mmol) of 2-ethoxy-1-ethoxycarbonyl-1,2dihydroquinoline is added at 0° C. It is stirred for 30 minutes at 0° C, then overnight at room temperature. It is evaporated to dryness in a vacuum and the residue is chromatographed on silica gel (mobile solvent: hexane/ethyl acetate 20:10:1).

Yield: 7.99 g (88% of theory) of a colorless solid
Elementary analysis: Cld: C 70.67 H 11.50 N 4.99 Fnd: C 70.78 H 11.60 N 4.83 b) 3,9-Bis(carboxymethyl)-6-bis(octadecyl)-aminocarbonylmethyl-3,6,9-triazaundecanedioic acid 5 g (4.46 mmol) of the title compound of Example 13a) is dissolved in 100 ml of trifluoroacetic acid and stirred overnight at room temperature. It is evaporated to dryness in a vacuum and the residue is chromatographed on silica gel (mobile solvent: methylene chloride/ethanol/33% ammonia water 20:5:0.5). The fractions containing the product are evaporated to dryness in a vacuum and the residue is dissolved in a mixture of 80 ml of ethanol/20 ml of water/30 ml of chloroform. 20 ml of acid ion exchanger IR 120 ($H^+$ form) is added and stirred for 30 minutes. It is filtered off from the ion exchanger and the filtrate is evaporated to dryness in a vacuum.

Yield: 2.67 g (65% of theory) of a glass-like solid
Water content: 2.7%
Elementary analysis (relative to anhydrous substance): Cld: C 67.11 H 10.90 N 7.57 Fnd: C 67.21 H 10.98 N 7.46

Example 14 a) Bis(octadecyl)-aminoacetic acid 30 g (57.47 mmol) of bis-octadecylamine and 8.38 g (60.3 mmol) of bromoacetic acid are dissolved in a mixture of 150 ml of toluene/10 ml of dioxane and refluxed overnight. 200 ml of 5% ammonia water is added and stirred for 10 minutes. The organic phase is separated, dried on magnesium sulfate and evaporated to dryness in a vacuum. The residue is chromatographed on silica gel (mobile solvent: methylene chloride/ethanol=20:1).

Yield: 20.33 g (61% of theory) of a waxy solid
Elementary analysis: Cld: C 78.69 H 13.38 N 2.41 Fnd: C 78.80 H 13.50 N 2.34 b) 1-[Bis(octadecyl)amino]-2-oxo-3-aza-13-aminotridecane 10 g (17.24 mmol) of the title compound of Example 14a) and 2.18 g (18.96 mmol) of N-hydroxysuccinimide are dissolved in 100 ml of dimethylformamide. It is cooled to 0° C. and 3.91 g (18.96 mmol) of dicyclohexylcarbodiimide is added. It is stirred for 1 hour at 0° C., then for 3 hours at room temperature. It is filtered off from precipitated urea and the filtrate is instilled within 30 minutes in a solution of 9.80 g (56.88 mmol) of diaminodecane and 5.76 g (56.88 mmol) of triethylamine in 200 ml of methylene chloride. It is stirred overnight at room temperature. It is evaporated to dryness in a vacuum, and the residue is dissolved in 200 ml of toluene. The organic phase is washed twice with 100 ml each of 5% aqueous soda solution, dried on magnesium sulfate and evaporated to dryness in a vacuum. The residue is chromatographed on silica gel (mobile solvent: methylene chloride/isopropanol/triethylamine=50:2:1).

Yield: 5.19 g (41% of theory) of a waxy solid
Elementary analysis: Cld: C 78.51 H 13.59 N 5.72 Fnd: C 78.61 H 13.68 N 5.60 c) 3,9-Bis(tert-butoxycarbonylmethyl)-6-[11-aza-13-bis(octadecyl)amino-12-oxo-tridecyl]aminocarbonylmethyl-3,6,9-triazaundecanedioic acid-di-tert-butyl ester 5 g (8.09 mmol) of the title compound of Example 11b) is dissolved in 25 ml of dimethylformamide, and 1.44 g (8.9 mmol) of N,N'-carbonyldiimidazole is added. It is stirred for 4 hours at room temperature. The solution is cooled off to 0° C., and a solution of 5.94 g (8.09 mmol) of the title compound of Example 14b) and 0.82 g (8.09 mmol) of triethylamine, dissolved in 50 ml of methylene chloride, is instilled within 30 minutes. It is stirred overnight at room temperature. It is evaporated to dryness, the residue is taken up in 150 ml of toluene and extracted twice with 100 ml each of 5% aqueous soda solution. The organic phase is dried on magnesium sulfate and concentrated by evaporation in a vacuum. The residue is chromatographed on silica gel (mobile solvent: methylene chloride/hexane/acetone= 20:10:1).

Yield: 8.42 g (78% of theory) of a waxy solid
Elementary analysis: Cld: C 70.22 H 11.48 N 6.30 Fnd: C 70.31 H 11.59 N 6.17 d) 3,9-Bis(carboxymethyl)-6-[11-aza-13-bis(octadecyl)amino-12-oxo-tridecyl]aminocarbonyl-methyl-3,6,9-triazaundecanedioic acid 5 g (3.75 mmol) of the title compound of Example 14c) is dissolved in 100 ml of trifluoroacetic acid and stirred overnight at room temperature. It is evaporated to dryness in a vacuum, and the residue is chromatographed on silica gel (mobile solvent: methylene chloride/ethanol/33% ammonia water 20:5:0.5). The fractions containing the product are evaporated to dryness in a vacuum and the residue is dissolved in a mixture of 80 ml of ethanol/20 ml of water/30 ml of chloroform. 15 ml of acid ion exchanger IR 120 ($H^+$ form) is added and stirred for 30 minutes. It is filtered off from the ion exchanger and the filtrate is evaporated to dryness in a vacuum.

Yield: 3.05 g (71% of theory) of a glass-like solid
Water content: 3.1%
Elementary analysis (relative to anhydrous substance): Cld: C 67.11 H 10.90 N 7.57 Fnd: C 67.21 H 10.98 N 7.46

Example 15 a) 3,9-Bis(tert-butoxycarbonylmethyl)-6-[3-aza-4-oxo-heneicosyl)-aminocarbonylmethyl-3,6,9-triazaundecanedioic acid-di-tert-butyl ester 5 g (7.58 mmol) of the title compound of Example 11c) and 2.30 g (22.73 mmol) of triethylamine are dissolved in 40

35 ml of methylene chloride. At 0° C., a solution of 2.53 g (8.34 mmol) of octadecanoic acid chloride in 20 ml of methylene chloride is instilled within 20 minutes. It is stirred overnight at room temperature. It is extracted with 50 ml of 5% aqueous salt solution, the organic phase is dried on magnesium sulfate and evaporated to dryness. The residue is chromatographed on silica gel (mobile solvent: methylene chloride/hexane/isopropanol=20:10:1).

Yield: 6.39 g (91% of theory) of a waxy solid

Elementary analysis: Cld: C 64.83 H 10.34 N 7.56 Fnd: C 64.73 H 10.40 N 7.48 b) 3,9-Bis(carboxymethyl)-6-[3-aza-4-oxo-heneicosyl)-aminocarbonylmethyl-3,6,9-triazaundecanedioic acid 5 g (5.4 mmol) of the title compound of Example 15a) is dissolved in 100 ml of trifluoroacetic acid and stirred overnight at room temperature. It is evaporated to dryness in a vacuum, and the residue is chromatographed on silica gel (mobile solvent: methylene chloride/ethanol/33% ammonia water 20:5:0.5). The fractions containing the product are evaporated to dryness in a vacuum, and the residue is dissolved in a mixture of 80 ml of ethanol/20 ml of water/30 ml of chloroform. 15 ml of acid ion exchanger IR 120 ($H^+$ form) is added and stirred for 30 minutes. It is filtered off from the ion exchanger, and the filtrate is evaporated to dryness in a vacuum.

Yield: 2.51 g (64% of theory) of a glass-like solid

Water content: 3.5%

Elementary analysis (relative to anhydrous substance): Cld: C 58.18 H 9.05 N 9.98 Fnd: C 58.03 H 9.14 N 9.89

Example 16 a) 3,9-Bis(tert-butoxycarbonylmethyl)-6-(10-carboxydecyl)-aminocarbonylmethyl-3,6,9-triazaundecanedioic acid-di-tert-butyl ester 5 g (8.09 mmol) of the title compound of Example 11b) and 0.82 g (8.09 mmol) of triethylamine are dissolved in 50 ml of methylene chloride. At −10° C., a solution of 1.10 g (8.09 mmol) of isobutyl chloroformate in 20 ml of methylene chloride is instilled within 5 minutes and stirred for 20 minutes at −10° C. The solution is cooled off to −15° C., and a solution of 1.63 g (8.09 mmol) of 11-aminoundecanoic acid and 2.43 g (24 mmol) of triethylamine in 50 ml of methylene chloride is instilled within 10 minutes and stirred for 30 minutes at −15° C., then overnight at room temperature. It is extracted twice with 100 ml each of 10% aqueous ammonium chloride solution, the organic phase is dried on magnesium sulfate and evaporated to dryness in a vacuum. The residue is chromatographed on silica gel (mobile solvent: methylene chloride/ethanol=20:1).

Yield: 4.41 g (68% of theory) of a colorless solid

Elementary analysis: Cld: C 61.47 H 9.56 N 6.99 Fnd: C 61.53 H 9.48 N 6.89 b) 3,9-Bis(carboxymethyl)-6-(10-carboxydecyl)-aminocarbonylmethyl-3,6,9-triazaundecanedioic acid 4 g (4.99 mmol) of the title compound of Example 16a) is dissolved in 100 ml of trifluoroacetic acid. It is stirred overnight at room temperature. It is evaporated to dryness in a vacuum, and the residue is chromatographed on silica gel (mobile solvent: ethanol/25% ammonia water 20:1). The fractions containing the product are evaporated to dryness in a vacuum. The residue is dissolved in 100 ml of water. 16 ml of acid ion exchanger IR 120 ($H^+$ form) is added and stirred for 10 minutes at room temperature. It is filtered off from the ion exchanger and evaporated to dryness in a vacuum.

Yield: 1.95 g (63% of theory) of a vitreous solid

Water content: 6.8%

36

Elementary analysis (relative to anhydrous substance): Cld: C 52.07 H 7.69 N 9.72 Fnd: C 52.15 H 7.60 N 9.64

What is claimed is:

1. A process for the production of a diethylenetriaminepentacarboxylic acid monoamide of formula (I)

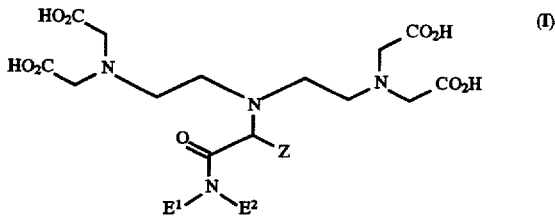

in which

Z, $E^1$, and $E^2$ independently of one another, each stand for a hydrogen atom or a saturated or unsaturated, branched or straight-chain $C_1$–$C_{50}$ alkyl chain, wherein:

the chain or parts of this chain optionally form a cyclic $C_5$–$C_8$ unit or a bicyclic $C_{10}$–$C_{14}$ unit;

the alkyl chain optionally contains 0 to 10 oxygen or 0 to 2 sulfur atoms, 0 to 3 carbonyl, 0 to 1 thiocarbonyl, 0 to 2 imino, 0 to 2 phenylene, 0 to 1 3-indole, 0 to 1 methyl-imidazol-4-yl, 0 to 3 N—$R^3$ groups or combinations thereof; and the alkyl chain is further optionally substituted by 0 to 2 phenyl, 0 to 2 pyridyl, 0 to 5 $R^2O$, 0 to 1 HS, 0 to 4 $R^2OOC$, 0 to 4$R^2OOC$—$C_{1-4}$ alkyl, 0 to 1 $R^2(H)N$ groups or combinations thereof, in which optionally present aromatic groups are optionally substituted zero to five times, independently of one another, by fluorine, $R^2O_2C$, $R^2OOC$—$C_{1-4}$ alkyl, $R^2(H)N$, $C_{1-4}$ alkyl—NH, $R^2NHOC$, $R^2CONH$, $O_2N$, $R^2O$, $R^2$ groups or combinations thereof, $R^2$ independently of one another, each stand for a hydrogen atom or a straight-chain or branched $C_1$–$C_4$ alkyl radical and $R^3$ independently of one another, each stand for a hydrogen atom or a straight-chain or branched, saturated or unsaturated $C_1$–$C_{30}$ alkyl radical or $E^1$ and $E^2$ together with inclusion of the nitrogen atom, are optionally a five- to eight-membered, saturated or unsaturated heterocycle, which optionally contains one to two additional nitrogen, oxygen, sulfur atoms, carbonyl groups or combinations thereof, in which the HO, $H_2N$, HS and HOOC group(s) optionally contained in $E^1$ or $E^2$ are optionally present in protected form and in which free carboxylic acid groups not used for complexing are optionally present as salts of the acid groups with physiologically compatible inorganic or organic cations or as esters or amides of the acid groups, which comprises reacting, in the presence of an organic solvent at a temperature of −10° C. to 50° C. a partially protected diethylenetriaminepentacarboxylic acid compound according to formula II

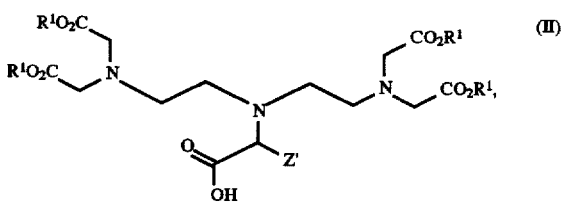

in which $R^1$ stands for a tert-butyl group or a benzyl group and Z' has the meaning of an optionally protected group Z, in which Z has the above-mentioned meaning, optionally with the addition of an activating reagent, with an amine of formula III

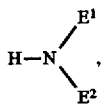 (III)

in which E¹ and E² have the above-mentioned meaning, and then producing the free acid of formula I by selective and mild cleavage of group R¹, as well as the protective groups (s) optionally contained in Z'.

2. The process according to claim 1, wherein at least one of radicals E¹ and E² stands for hydrogen or a methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, or n-icosyl radical.

3. The process according to claim 1, wherein at least one of radicals E¹ and E² stands for a 2-hydroxyethyl chain or for a radical of formula IV

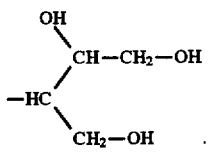 (IV)

4. The process according to claim 1, wherein at least one of radicals E¹ and E² stands for a radical

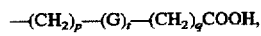

in which
G stands for oxygen or sulfur,
p and q independently of one another, stand for a number of from 1 to 18,
t stands for 0 or 1, and p+t+q≦20, where the acid group is optionally present as a salt of the acid with an inorganic or organic base, as an ester of the acid or as an amide of the acid.

5. The process according to claim 1, wherein at least one of radicals E¹ and E² stands for a radical

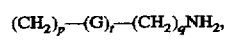

in which
G stands for oxygen or sulfur,
p and q independently of one another, stand for a number of from 1 to 18,
t stands for 0 or 1,
and p+t+q≦20, wherein the amino group is optionally present as an ammonium salt with a physiologically compatible anion or as an amide.

6. The process according to claim 1, wherein Z stands for the methyl, ethyl, propyl, i-propyl, butyl, i-butyl, tert-butyl, pentyl, hexyl, or cyclohexyl radical.

7. The process according to claim 1, wherein Z stands for a phenyl or benzyl radical, which optionally is substituted zero to five times, independently of one another, by F, HO, R²O, R², H₂N, R²CONH, R²NHCO, O₂N, HOOC or R²OOC groups, in which R² stands for a branched or unbranched C₁–C₄ alkyl radical.

8. The process of claim 1, wherein Z is a group of one of the following formulae:

−H
−CH₃
−CH(CH₃)₂
−CH₂−CH(CH₃)₂
−CH₂−Ph
−CH₂OH
−CH(OH)−CH₃
−CH₂SH
−CH₂−SCH₃
−CH₂CO₂H
−CH₂CH₂−CO₂H
−(CH₂)₄−NH₂

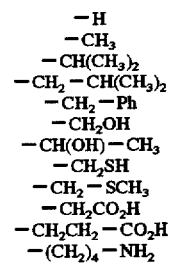

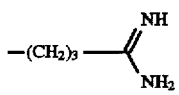

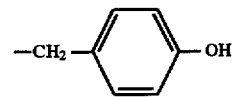

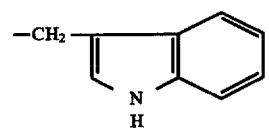

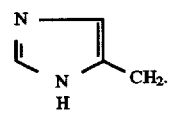

9. Process according to claim 8, wherein the amino acid is glycine, alanine, valine, leucine, phenylalanine, tyrosine, serine, threonine, cysteine, methionine, tryptophane, aspartic acid, glutamic acid, arginine, lysine or histidine.

10. Process according to claim 1, wherein R¹ stands for a benzyl group and the cleavage of this group R¹ takes place by hydrogenolysis.

11. Process according to claim 1, wherein R¹ stands for a tert-butyl group and the cleavage of this group R¹ takes place by saponification with trifluoroacetic acid.

12. The process of claim 1, wherein an activating reagent is present in the reaction of the partially protected diethylenetriaminepentacarboxylic acid compound of formula (II) with the amine of formula (III).

13. The process of claim 12, wherein the activating reagent is provided by the reaction of acid with dicyclohexylcarbodiimide, N-hydroxysuccinimide/dicyclohexylcarbodiimide, carbonyldiimidazole, 2-ethoxy-1-ethoxycarbonyl-1,2-dihydroquinoline, oxalic acid dichloride or isobutyl chloroformate.

14. The process of claim 1, wherein the reaction of the partially protected diethylenetriaminepentacarboxylic acid compound of formula (II) with the amine of formula (III) is conducted in the absence of a chlorinated solvent.

* * * * *